United States Patent
Tesson et al.

(10) Patent No.: US 9,738,607 B2
(45) Date of Patent: Aug. 22, 2017

(54) SCALABLE PROCESS FOR THE PREPARATION OF SORAFENIB TOSYLATE ETHANOL SOLVATE AND SORAFENIB TOSYLATE FORM III

(71) Applicant: F.I.S.—FABBRICA ITALIANA SINTETICI S.P.A, Montecchio Maggiore (VI) (IT)

(72) Inventors: Nicolas Tesson, L'Hospitalet de Llobregat (ES); Carmen Jiménez, Sant Climent de Llobregat (ES); Llorenç Rafecas, Llorenç del Penedès (ES); Marta Pontini, Montebelluna (ES)

(73) Assignee: F.I.S.—FABBRICA ITALIANA SINTETICI S.P.A., Montecchio Maggiore (VI) (IT)

(*) Notice: Subject to any disclaimer, the term of this patent is extended or adjusted under 35 U.S.C. 154(b) by 0 days.

(21) Appl. No.: 15/215,782

(22) Filed: Jul. 21, 2016

(65) Prior Publication Data

US 2016/0376236 A1  Dec. 29, 2016

(30) Foreign Application Priority Data

Jun. 23, 2015 (EP) .................................... 15173282

(51) Int. Cl.
| | | |
|---|---|---|
| C07C 309/30 | (2006.01) | |
| C07C 31/08 | (2006.01) | |
| A61K 31/44 | (2006.01) | |
| A61K 47/48 | (2006.01) | |
| C07D 213/81 | (2006.01) | |

(52) U.S. Cl.
CPC ............ *C07D 213/81* (2013.01); *A61K 31/44* (2013.01); *A61K 47/48023* (2013.01); *C07C 31/08* (2013.01); *C07C 309/30* (2013.01)

(58) Field of Classification Search
CPC .................................................... C07D 213/81
USPC ........................................................ 514/346
See application file for complete search history.

(56) References Cited

FOREIGN PATENT DOCUMENTS

| | | |
|---|---|---|
| EP | 1140840 B1 | 3/2006 |
| EP | 1797038 B1 | 6/2012 |
| WO | 0042012 A1 | 7/2000 |
| WO | 2006034796 A1 | 4/2006 |
| WO | 2006034797 A1 | 4/2006 |
| WO | 2009092070 A1 | 7/2009 |
| WO | 2013175506 A2 | 11/2013 |
| WO | 2013175506 A3 | 6/2014 |
| WO | 2014118807 A1 | 8/2014 |

OTHER PUBLICATIONS

Ethyl Alcohol Handbook, 6th Edition, 2003, Equistar Chemicals, Houston, Texas.*
European Search Report for European Application No. 15173282 (dated Sep. 3, 2015) (4 pages).
Sorbera et al., "BAY-43/9006. Oncolytic, Raf Kinase Inhibitor", Drugs of the Future, 2002, vol. 27, No. 12, pp. 1141-1147.

(Continued)

*Primary Examiner* — Daniel Carcanague
(74) *Attorney, Agent, or Firm* — Lucas & Mercanti, LLP

(57) ABSTRACT

The present invention refers to an improved process for the preparation of Sorafenib tosylate ethanol solvate and Sorafenib tosylate form III.

18 Claims, 4 Drawing Sheets

(56) References Cited

OTHER PUBLICATIONS

Teasdale et al., "Risk Assessment of Genotoxic Impurities in New Chemical Entities: Strategies to Demonstrate Control", Organic Process Research & Development, 2013, vol. 17, pp. 221-230.
Bankston et al., "A Scalable Synthesis of BAY 43/9006: A Potent Raf Kinase Inhibitor for the Treatment of Cancer", Organic Process Research & Development, 2002, vol. 6, No. 6, pp. 777-781.

* cited by examiner

EP1797038

WO2009/092070

WO2014/118807

Base = Sorafenib base
TS = Sorafenib tosylate
hemi-TS = sorafenib hemitosylate
Ex. = example

SCALABLE PROCESS FOR THE PREPARATION OF SORAFENIB TOSYLATE ETHANOL SOLVATE AND SORAFENIB TOSYLATE FORM III

CROSS-REFERENCE TO RELATED APPLICATIONS

This application claims the benefit of priority from European Patent Application No 15173282.3 filed Jun. 23, 2015, the contents of which are incorporated herein by reference.

TECHNICAL FIELD

The present invention refers to an improved process for the preparation of Sorafenib tosylate ethanol solvate and Sorafenib tosylate form III.

BACKGROUND OF THE INVENTION

Sorafenib is an active pharmaceutical ingredient approved for the treatment of the primary kidney cancer, for the treatment of advanced primary liver cancer and radioactive iodine resistant advanced thyroid carcinoma.

Sorafenib, also named BAY 43-9006 and abbreviated SRFB, is marketed in form of tosylate salt, in particular, in form of monotosylate salt, i.e. a salt made by one molecule of paratoluensulfonic acid per one molecule of Sorafenib.

Sorafenib tosylate is a non-chiral molecule having the following formula (I):

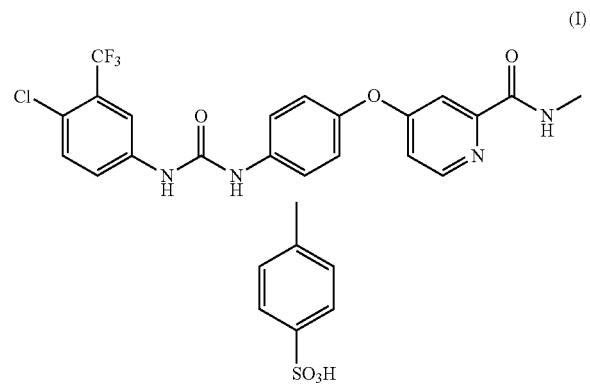

(I)

and has chemical name 4-[4-({[4-chloro-3-(trifluoromethyl)phenyl]carbamoyl}amino)phenoxy]-N-methylpyridine-2-carboxamide 4-methylbenzenesulfonate (1:1).

The synthesis of Sorafenib was disclosed in detail in the patent publication EP1140840, in Organic Process Research & Development (OPRD), 2002, 6, 777-781, in Drug of the Future (2002), 27(12), 1141-1147 and in OPRD, 2013, 17(2), 221.

The synthesis disclosed in patent EP1140840, named Route A, particularly in examples A2, B1 and C1a, appears an attractive route of synthesis for the preparation of Sorafenib.

The later publication WO2006034796 discloses the industrial synthesis of Sorafenib on multi Kgs scale wherein specific conditions to perform the coupling step are disclosed in detail. Method 5a discloses the preparation of Sorafenib tosylate form I, i.e. Sorafenib tosylate having crystalline or polymorphic form named form I.

The active pharmaceutical substance Sorafenib tosylate shows polymorphism and many crystal forms are currently known.

In the patent publication EP1797038 the applicant states that the polymorph included in the marketed pharmaceutical composition is the thermodynamically stable polymorph, i.e. the polymorph having melting point 223-231° C., also named form I or polymorph I.

In the same document EP1797038 are disclosed and well characterized other solid forms of Sorafenib, in particular:

Sorafenib tosylate form II, having m.p. 194° C., being a metastable form,

Sorafenib tosylate form III, having m.p. 187-190° C.,

Sorafenib tosylate methanol solvate, that loses 4.8% by weight in TGA,

Sorafenib tosylate ethanol solvate, that loses 6.7% by weight in TGA.

According to the teaching of EP1797038, par. 6, the crystalline form or polymorph named form II was already part of the state of the art since it was first disclosed in example 1 of WO00/42012.

In particular EP1797038 discloses the preparation of Sorafenib tosylate form I treating with an inert solvent Sorafenib tosylate form II from 50° C. up to reflux temperature. The working example 2 provides some procedures for the conversion of form II to form I.

Sorafenib tosylate form II was prepared in example 1 of EP1797038 starting from Sorafenib base.

The publication EP1797038 also discloses a method for the preparation of Sorafenib tosylate form III treating Sorafenib tosylate form II with an inert solvent, e.g. with methanol. Filtration is performed after from 1 day to 1 week, and the product is dried and heat-treated at from 145° C. to 160° C. for from 15 minutes to 1 hour. Working example 3 provides an embodiment of the said conversion of form II to form III by slurring form II in methanol for one week at room temperature.

The publication EP1797038 discloses a method for the preparation of Sorafenib tosylate ethanol solvate treating Sorafenib tosylate form II with ethanol. Filtration is performed after 1 week, and the product is dried. Working example 5 provides an embodiment of such conversion of form II to Sorafenib tosylate ethanol solvate by slurring form II in ethanol for one week at room temperature. After filtration, the product was dried at room temperature.

Sorafenib tosylate ethanol solvate has the following formula (I-EtOH):

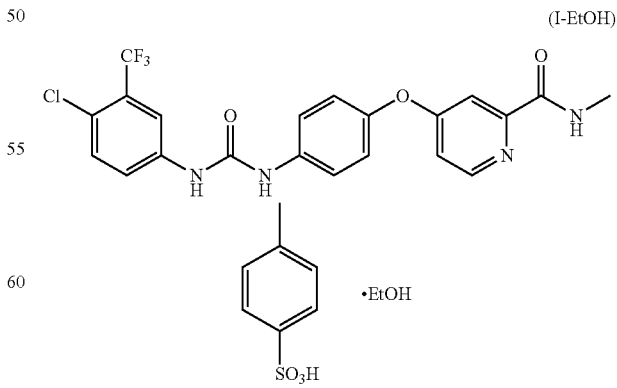

(I-EtOH)

and has chemical name 4-[4-({[4-chloro-3-(trifluoromethyl)phenyl]carbamoyl}amino)phenoxy]-N-methylpyridine-2- carboxamide 4-methylbenzenesulfonate, compound with ethanol (1:1:1) or 2-Pyridinecarbaxamide, 4-[4-[[[[4-chloro-3-(trifluoromethyl)phenyl]amino]carbonyl]amino]phenoxy]-N-methyl-, 4-methylbenzenesulfonate, compound with ethanol (1:1:1).

The biggest drawback of the above described procedure for the preparation of Sorafenib tosylate form III and Sorafenib tosylate ethanol solvate is that the starting material for said procedure, i.e. Sorafenib tosylate form II is a metastable form, as declared in EP1797038 itself. Indeed, according to our experimentations, once Sorafenib toyslate form I is obtained for the first time, it is not more possible to produce Sorafenib tosylate form II. Therefore, the methods disclosed in EP1797038 for the preparation of Sorafenib tosylate form III and Sorafenib tosylate ethanol solvate, are not suitable for routine preparations of said compounds and are not scalable for larger productions, indeed it would be extremely difficult to obtain and to maintain the form II and therefore to control its conversion to form III.

The publication WO2009/092070 discloses in the working examples 2-4 the preparation of Sorafenib tosylate methanol solvate by treating a solution of Sorafenib base in methanol or in NMP with a methanolic solution of paratoluenesulfonic acid monohydrate.

The publication WO2009/092070 also discloses in the working example 5 the preparation of Sorafenib tosylate methanol solvate by treating a solution of Sorafenib tosylate form I in a mixture of DMSO and methanol with paratoluenesulfonic acid monohydrate.

Example 6 of WO2009/092070 is particularly important since it discloses for the first time the preparation of Sorafenib tosylate form III by treating Sorafenib tosylate methanol solvate at 80° C. under vacuum for 16 hours.

Example 7 of WO2009/092070 discloses the preparation of Sorafenib tosylate ethanol solvate by stirring a suspension of Sorafenib toyslate form III in ethanol for 48 hours.

Example 8 and 11 and examples 9, 10, 12 of WO2009/092070 disclose for the first time the preparation of Sorafenib hemi-tosylate respectively from Sorafenib tosylate form III in water or from Sorafenib base in isopropanol, n-propanol or acetone. When Sorafenib hemi-tosylate is prepared from Sorafenib base, paratoluensulfonic acid monohydrate was added.

The publication WO2014/118807 in examples 1 and 2 discloses a method for the preparation of Sorafenib tosylate ethanol solvate by addition of paratoluensulfonic acid monohydrate to a suspension of Sorafenib base in ethanol and further stirring for respectively 7 or 3 days.

Then Sorafenib tosylate form III was obtained by drying under vacuum at 80-85° C. for 20-22 hours Sorafenib tosylate ethanol solvate.

Both the experiments 1 and 2 of WO2014/118807 have been reworked using absolute ethanol and it was observed that in both the experiments 1 and 2, after 10 minutes by the end of the addition of paratoluensolfonic acid, Sorafenib tosylate form I was obtained substantially in quantitative manner. Then, stirring form I in absolute ethanol for at least 6 days (not before since for example after only 5 days there are residual amounts of form I) Sorafenib tosylate ethanol solvate is obtained.

It is thus clear that the procedure disclosed in WO2014/118807 starts from Sorafenib base, then is produced Sorafenib tosylate form I which is slowly converted in ethanol into Sorafenib tosylate ethanol solvate. Therefore said procedure thus passes through the transient specie being Sorafenib tosylate form I which is formed in situ and slowly converts to Ethanol solvate form.

Sorafenib tosylate ethanol solvate obtained according to the experiments 1 or 2 of WO2014/118807, i.e. prepared by a process wherein Sorafenib tosylate form I is appeared, although as transient form, does not provide polymorphic pure Sorafenib tosylate form III.

Indeed, performing the step II of experiments 1 and 2 of WO2014/118807, using Sorafenib tosylate ethanol solvate prepared in step I, the Sorafenib tosylate form III thus prepared is contaminated by form I.

Moreover, the problem due to the presence of the form I as impurity of the form III is magnified by increasing the scale, indeed just a sample of about 5 grams of Sorafenib tosylate ethanol solvate (as in example 1 WO2014/118807) can be dried/converted in form III at 80-85° C. in 20-22 hours, since the preparation of form III, for example at Klab scale, requires much higher temperature to complete the conversion of Sorafenib tosylate ethanol solvate into Sorafenib tosylate form III in reasonable time. To the other side, high temperature promotes the conversion of Sorafenib tosylate form III into Sorafenib tosylate form I (the form thermodynamically stable) especially when Sorafenib tosylate form III contains little amounts, traces or also microseedings of Sorafenib tosylate form I.

Thus, with the aim of preparing Sorafenib tosylate form III with a scalable process that can be also applied for industrial productions, it is mandatorily essential to set up a process for preparing Sorafenib tosylate form III which avoid absolutely and completely the appearance of Sorafenib tosylate form I.

Finally, Sorafenib tosylate form III as prepared have to comply with the stability stress studies which includes the study of the prolonged stability at high temperature. To this aim it is essential that Sorafenib tosylate form III does not contain any microseed or microcrystal of form I otherwise that seed triggers and catalyzes the conversion of form III to form I.

The "stability stress" requirements can be satisfied only if in the process for the preparation of sorafenib tosylate form III and related precursor intermediate Sorafenib tosylate ethanol solvate, there is not appearance of Sorafenib tosylate form I.

In other words, avoiding the appearance of Sorafenib tosylate form I during a process for the preparation of Sorafenib form III and intermediates thereof, e.g. during the preparation of Sorafenib tosylate ethanol solvate, it can be produced Sorafenib tosylate form III with increased stability towards the conversion to the termodinamically stable form being Sorafenib tosylate form I.

SUMMARY OF THE INVENTION

The problem addressed by the present invention is therefore that of providing an improved scalable process for the preparation of Sorafenib tosylate ethanol solvate and Sorafenib tosylate form III without the appearance of the thermodynamically stable Sorafenib tosylate form I.

As said above, it has been observed that if during the preparation of Sorafenib tosylate ethanol solvate, Sorafenib tosylate form I is formed, then the remaining traces or microseeds of Sorafenib tosylate form I into Sorafenib tosylate ethanol solvate catalyze the formation of said form I so that pure crystalline form III of Sorafenib tosylate cannot be prepared.

It has been indeed observed that when converting Sorafenib Ethanol solvate prepared with a process wherein Sorafenib tosylate form I is formed as transient intermediate specie before providing Sorafenib Ethanol solvate, then Sorafenib tosylate form III contains Sorafenib tosylate form I as impurity.

Therefore, it is desirable a process for the preparation of Sorafenib tosylate ethanol solvate and then Sorafenib tosylate form III which is scalable in industrial plant without the appearance of Sorafenib tosylate form I.

As additional related problem, it is desirable that the process for the preparation of Sorafenib tosylate form III from Sorafenib tosylate ethanol solvate allows the preparation of pure polymorphic form III.

Finally, a faster process for the preparation of Sorafenib tosylate form III is also an objective of the present invention.

These problems are solved by a process for the preparation of Sorafenib tosylate ethanol solvate and then Sorafenib tosylate form III as outlined in the annexed claims, whose definitions are integral part of the present description.

Further features and advantages of the process according to the invention will result from the description hereafter reported of examples of realization of the invention.

DRAWINGS

DETAILED DESCRIPTION OF THE INVENTION

Figure 1:
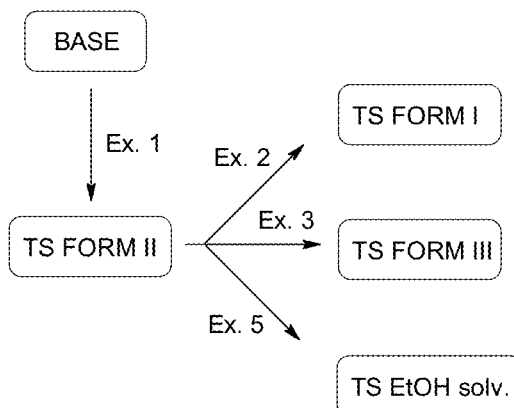
FIG. 1 shows a comprensive exemplificative scheme of the state of the art of the solid forms of Sorafenib tosylate and conversions thereof.
Figure 1:
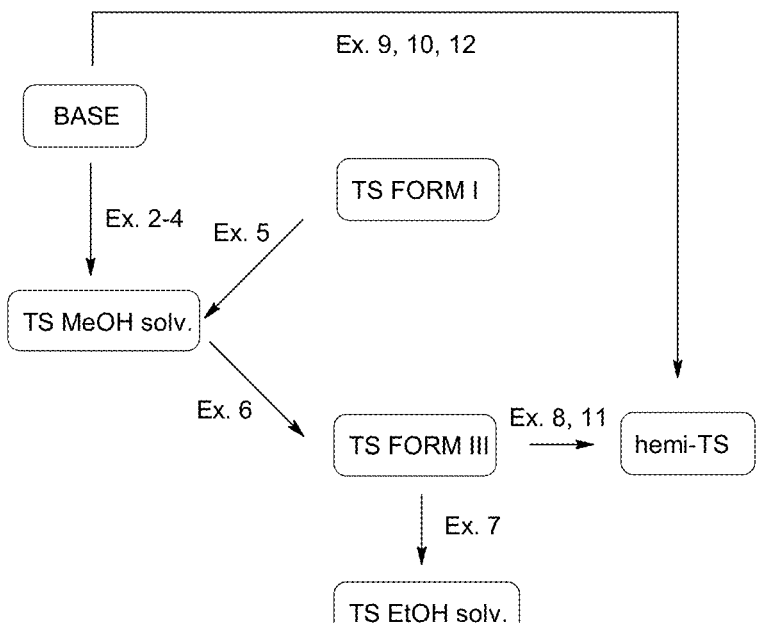
Figure 1:
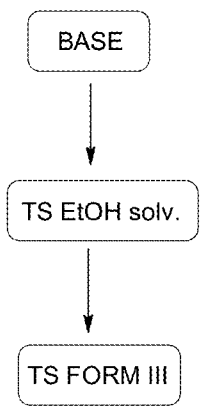

Preliminary experimental attempts to obtain Sorafenib tosylate ethanol solvate directly from Sorafenib (free) base without contamination by the Sorafenib tosylate form I, contamination in the final product or intermediate contamination during the process, failed.

The formation of Sorafenib tosylate form I is indeed kinetically favored even in the presence of Sorafenib tosylate ethanol solvate seeding.

After a lot of experimental work, it has been found a process for the preparation of Sorafenib tosylate ethanol solvate of formula (I-EtOH):

(I-EtOH)

comprising the following steps:
a) providing a suspension of Sorafenib hemi-tosylate of formula (II) or hydrates thereof:

(II)

in ethanol 90-95% v/v,
b) adding paratoluensulfonic acid or hydrates thereof to the suspension of the step a),
c) stirring,
d) isolating the product Sorafenib tosylate ethanol solvate of formula (I-EtOH).

It was indeed found that the conversion of Sorafenib hemi-tosylate into Sorafenib tosylate ethanol solvate, in presence of paratoluensolfonic acid (abbreviated TsOH), in EtOH 90-95% v/v led to the desired Sorafenib tosylate ethanol solvate without contamination and without the appearance/disappearance of Sorafenib tosylate form I.

In the step a) the provision of a suspension of Sorafenib hemi-tosylate of formula (II) or hydrates thereof means that said suspension can be prepared suspending isolated compound (II) or hydrates thereof in ethanol 90-95% v/v or, alternatively, preparing the compound (II) or hydrates thereof in ethanol 90-95% v/v.

The ethanol 90-95% v/v means a solution consisting in 90-95 parts in volumes of ethanol and 10-5 parts in volumes of water. Thus, e.g., ethanol 95% v/v means a mixture of 95 ml of ethanol (absolute) and 5 ml of water.

The addition of paratoluensulphonic acid or hydrates thereof to the suspension of the step a) can be performed adding solid of paratoluensulfonic acid or hydrates thereof or adding a solution of paratoluensulfonic acid or hydrates thereof.

The paratoluensulfonic acid or p-toluensulfonic acid is commonly abbreviated as TsOH and paratoluensulfonic acid monohydrate is abbreviated TsOH.H$_2$O.

According to one preferred embodiment of the invention the hydrate of Sorafenib hemi-tosylate of formula (II) is Sorafenib hemi-tosylate monohydrate.

According to one preferred embodiment of the invention, step a) can be carried out starting from isolated Sorafenib hemi-tosylate or hydrated thereof.

According to a more preferred embodiment of the invention, step a) can be carried out starting from isolated Sorafenib hemitosylate monohydrate.

According to an alternative embodiment of the step a) the provision of a suspension of Sorafenib hemi-tosylate of formula (II) or hydrates thereof can be realized by preparing the compound (II) or hydrates thereof in ethanol 90-95% v/v.

According to a more preferred embodiment of the invention, in the step a) the provision of a suspension of Sorafenib hemi-tosylate of formula (II) or hydrates thereof is carried out by adding paratoluensulphonic acid or hydrates thereof to a solution of Sorafenib base of formula (III):

(III)

[Chemical structure of Sorafenib base]

in ethanol 90-95% v/v.

Thus, another aspect of the present invention is a process for the preparation of Sorafenib hemi-tosylate of formula (II) or hydrates thereof:

(II)

[Chemical structure of Sorafenib hemi-tosylate with ·1/2 p-toluenesulfonic acid]

by addition of paratoluensulphonic acid or hydrates thereof to a solution of Sorafenib base of formula (III):

(III)

[Chemical structure of Sorafenib base]

in ethanol 90-95% v/v.

Said process allows the preparation Sorafenib hemi-tosylate of formula (II) or hydrates thereof without the appearance of Sorafenib tosylate form I, thus is suitable for the preparation of Sorafenib tosylate ethanol solvate or Sorafenib tosylate form III stable toward the conversion to Sorafenib tosylate form I, according to the process of the present invention.

According to a preferred embodiment of the invention, the step b) can be carried out adding at room temperature an ethanol solution (90-95% v/v) of TsOH to a suspension of Sorafenib hemi-tosylate in ethanol 90-95% v/v.

According to a preferred embodiment of the invention, the step a) can be carried out by in situ preparation of Sorafenib hemi-tosylate monohydrate of formula (II) staring from Sorafenib free base of formula (III) in ethanol 90-95% v/v by addition of paratoluensolfonic acid or hydrates thereof.

According to a preferred embodiment of the invention, the step a) can be carried out by in situ preparation of Sorafenib hemi-tosylate from Sorafenib base of formula (III) wherein said steps are carried out in a one-pot process, without the isolation of the compound Sorafenib hemi-tosylate of formula (II) or hydrates thereof.

The crystalline transformation can be monitored by DSC and/or XRPD in order to control both objectives of the process:
  total conversion of hemitosylate to Sorafenib tosylate ethanol solvate,
  absence of Sorafenib tosylate form I during the whole process.

The mixture can be analyzed after the addition, and then after each hour.

This monitoring by DSC is important because Sorafenib tosylate form I could appear as an intermediate transient crystalline form in the mixture, and then is converted to Sorafenib tosylate ethanol solvate so that only apparently crystalline pure Sorafenib tosylate ethanol solvate is recovered at the end of the reaction.

As general experimental observation, the treatment of Sorafenib tosylate form I in ethanol, especially in presence of TsOH, provides Sorafenib tosylate ethanol solvate since said form is the solid form thermodynamically favorite in ethanol environment.

The treatment of Sorafenib base with paratoluensolfonic acid in absolute ethanol, always provides Sorafenib tosylate form I.

Sorafenib tosylate form I is then converted into Sorafenib tosylate ethanol solvate by stirring in ethanol, preferably in presence of TsOH, similarly at what observed in WO2009/092070 example 5 for Sorafenib tosylate methanol solvate.

Thus, when Sorafenib hemi-tosylate is stirred in absolute ethanol and TsOH is added, Sorafenib tosylate form I appears as transient intermediate, which is then slowly converted in Sorafenib tosylate ethanol solvate.

It has been surprisingly found that the presence of a small amount of water is essential for preventing the appearance of Sorafenib tosylate form I, both as transient form or as a crystalline impurity of Sorafenib tosylate ethanol solvate. Moreover, it has been found that a high amount of water stabilizes Sorafenib hemi-tosylate leading to Sorafenib hemi-tosylate only contaminated with Sorafenib tosylate ethanol solvate or even pure Sorafenib hemi-tosylate.

Figure 3:
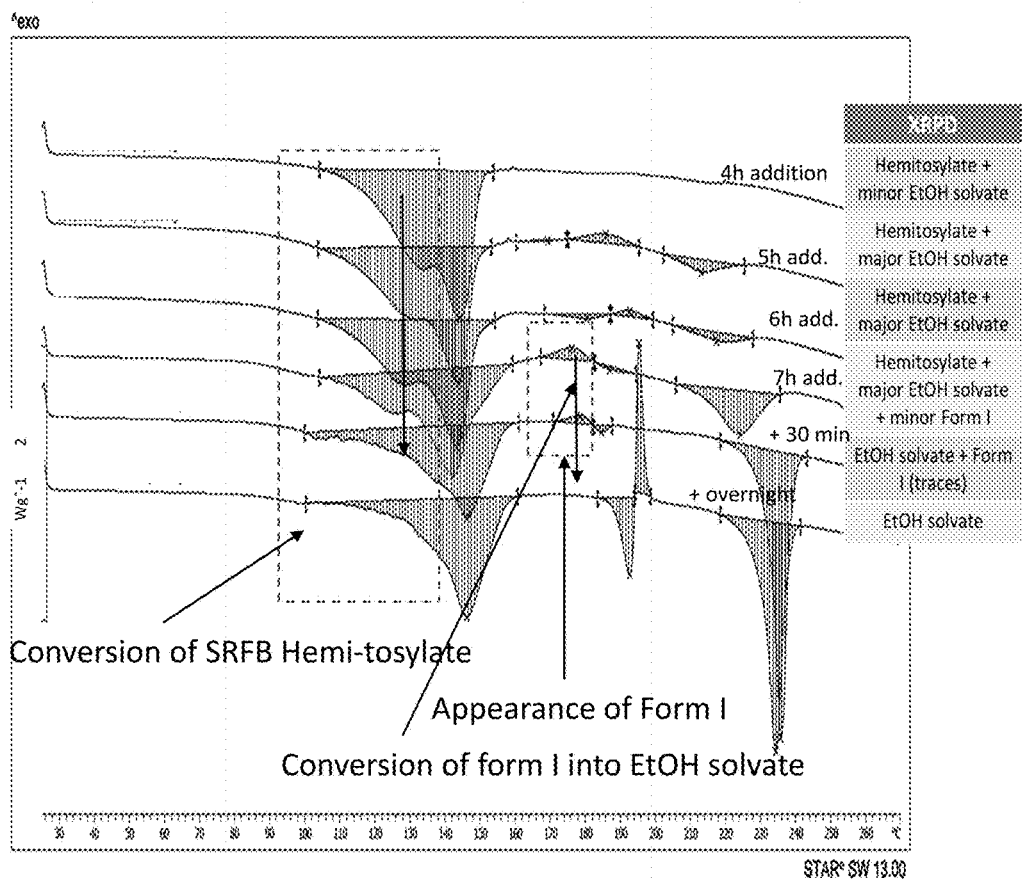
FIG. 3 shows the DSC curves monitoring the conversion of Sorafenib hemi-tosylate monohydrate to Sorafenib tosylate ethanol solvate using Ethanol 88% v/v.
Figure 4:
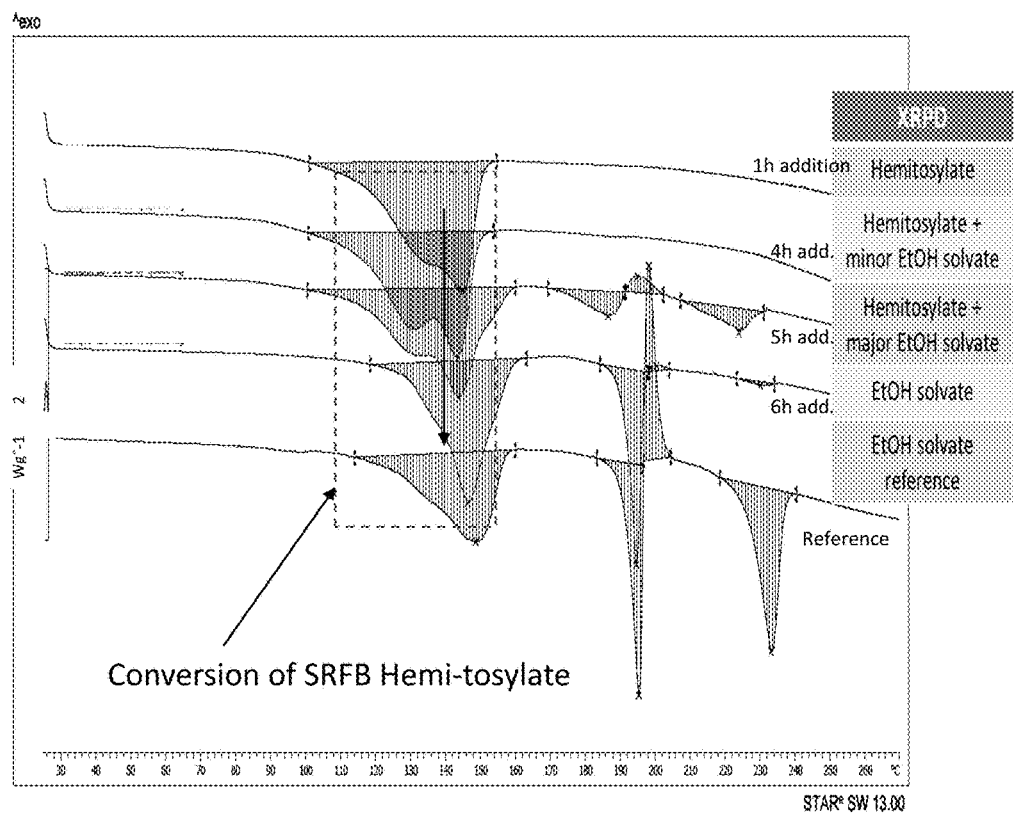
FIG. 4 shows the DSC curves monitoring the conversion of Sorafenib hemi-tosylate monohydrate to Sorafenib tosylate ethanol solvate using Ethanol 92% v/v.

It has thus found that ethanol 90-95% v/v, guarantees a complete conversion of Sorafenib hemi-tosylate or hydrate thereof to Sorafenib tosylate ethanol solvate without the appearance of Sorafenib tosylate form I as intermediate (see comparative FIGS. 3 and 4, wherein in FIG. 4 Ethanol 92% v/v was used, thus clearly showing the effect of the invention).

According to an embodiment of the present invention, the step a) or the steps from a) to d) are carried out in ethanol 90%-95% v/v.

According to a preferred embodiment of the present invention, the step a) or the steps from a) to d) are carried out in ethanol 91%-94% v/v, more preferably from 91% to 93% v/v, being 92% v/v the best value.

The process of the present invention can be carried out using in the step a) or in the steps from a) to d) from 5 to 20 volumes of Ethanol 90%-95% v/v compared with Sorafenib hemi-tosylate or hydrated thereof.

According to a preferred embodiment of the process of the present invention, in the step a) or in the steps from a) to d) are used from 7 to 17 volumes of ethanol 90-95% v/v compared with Sorafenib hemi-tosylate or hydrated thereof, more preferably from 8 to 10 volumes of ethanol, being 10 volumes the best value.

Starting from Sorafenib hemi-tosylate or hydrates thereof, in the step b) the amount of paratoluensulfonic acid added is from 0.7 to 3.0 equivalents, preferably from 0.7 to 1.2 equivalents, more preferably from 0.7 to 0.9 equivalents since they provide a complete conversion to Sorafenib tosylate ethanol solvate.

According to a preferred embodiment, in the step b) the addition of paratoluensulfonic is performed by adding at first from 0.3 to 0.8 equivalents and then, adding later the remaining paratoluensulfonic acid in one or more portions.

As another general experimental observation, to avoid the appearance of Sorafenib tosylate form I is important to avoid high local concentration of paratoluensolfonic acid.

To achieve said condition is possible and it is convenient to apply one or more of the following actions/conditions:
adding paratoluensolfonic acid very slowly,
adding paratoluensolfonic acid portionwise or in solution dropwise,
adding the paratoluensolfonic acid in solution,
using high stirring rates,
performing the addition of paratoluensolfonic acid inner to the solution instead of dropping it on the surface.

According to an embodiment of the invention, in the step b) the addition of paratoluensulfonic acid or hydrates thereof is carried out portionwise or dropwise in solution, since it helps to avoid the possible appearance of Sorafenib tosylate form I.

According to a preferred embodiment of the invention it is possible to add from 0.6 to 0.8 eq. of paratoluensolfonic acid at the begin of the reaction and then, if the conversion is not complete, to perform other additions of paratoluensolfonic acid when significant amount of Sorafenib tosylate ethanol solvate is already present in the reaction mixture.

According to an embodiment of the invention, after the first addition from 0.3 to 0.8 eq. of paratoluensolfonic acid, two or more further additions of 0.1 eq. TsOH solid can be performed to reach complete conversion.

According to a preferred embodiment of the invention the portionwise or dropwise addition of paratoluensulfonic acid can be done according the following manner:
0.6 eq. of TsOH in solution, 0.1 eq. of TsOH solid after 4-5 h and then 0.1 eq. after 0.5 h.

An additional amount of TsOH could be necessary in order to complete the conversion and should be added several hours after the initial addition in order to disfavor the appearance of Sorafenib tosylate form I.

After an initial addition of 0.3, 0.5 or 0.6 eq. of TsOH in solution in EtOH (90-95% v/v), additional amounts of TsOH can be added in portions until complete conversion. In particular, using portionwise or dropwise addition of TsOH, complete conversion was reached when a total of 0.7-0.9 eq. of TsOH was used, adding TsOH according to the following scheme:
0.5+0.1+0.1 eq.
0.6+0.1+0.1 eq.
0.3+0.3+0.3 eq.
0.7+0.3+0.1 eq.
0.8+0.2+0.1 eq.

Furthermore, it was checked that the addition of an excess of TsOH (+0.3 eq.) when the conversion was already complete did not lead to the formation of Sorafenib tosylate form I: Sorafenib tosylate ethanol solvate remained stable.

According to a preferred embodiment, the addition of paratoluensulphonic acid is carried out by performing an initial addition of 0.6 eq. of paratoluensulphonic, followed by another addition of 0.3 eq. paratoluensulphonic acid. Preferably, the second addition is performed two hours later than the first addition.

According to a more preferred embodiment, the addition of paratoluensulphonic acid is carried out by performing an initial addition of 0.6 eq. of paratoluensulphonic in solution in 1.5 vol. ethanol 90-95% v/v, followed by another addition of 0.3 eq. paratoluensulphonic acid in solution in 0.5 vol. EtOH 90-95% v/v two hours later.

Performing such additions, the reaction performed at 2 g scale afforded Sorafenib tosylate ethanol solvate with a good yield of 84%.

Furthermore, control of the transformation by XRPD indicated the absence of Sorafenib tosylate form I during the process.

In one experiment, 0.7 eq. of paratoluensulphonic acid were added in the initial addition, then the total conversion was obtained by the two further additions of paratoluensulphonic acid (0.3 and 0.1 eq.).

In order to obtain a more progressive conversion, 0.8 instead of 0.7 eq. of paratoluensulphonic acid was added in the initial addition. In this case, partial conversion was observed after 2 h. The subsequent addition of 0.2 eq. and 0.1 eq. of TsOH led to complete conversion without appearance of Sorafenib tosylate form I during the process.

This process was reproduced and scaled up to 5 g affording the same results.

According to a preferred embodiment of the invention, in the step b) the paratoluensulfonic acid is in solution of ethanol 90-95% v/v.

According to a preferred embodiment of the invention, in the step b) the paratoluensulfonic acid is solubilized in an amount of ethanol 90-95% v/v comprised between 1 and 5 volumes compared to the starting compound of formula (II), more preferably 2 volumes.

According to a more preferred embodiment of the invention in the step b) the addition of paratoluensulfonic acid in solution of ethanol 90-95% v/v is performed in a time comprised between 0.5 and 10 hours.

According to a preferred embodiment, when the process starts from Sorafenib base of formula (III), the step a) is carried out by addition of 1.3 equivalents of TsOH or hydrates thereof and step b) is carried out by addition of 1.2 equivalents of TsOH or hydrates thereof.

According to a more preferred embodiment, when the process starts from Sorafenib base of formula (III), the step a) is carried out by addition of 1.3 equivalents of TsOH or hydrates thereof in about 4 hours and step b) is carried out by addition of 1.2 equivalents of TsOH or hydrates thereof in about 4 hours.

The step c) can be carried out for at least the time necessary to complete the conversion of Sorafenib hemi-tosylate to Sorafenib tosylate ethanol solvate. Typically it takes from 1 to 48 hours.

According to a preferred embodiment of the invention, the step c) can be prolonged for a time comprised between 1 and 72 hours after the completation of the conversion of Sorafenib hemi-tosylate to Sorafenib tosylate ethanol solvate.

Indeed, longer stirring time, even if the reaction seems complete by DSC or XRPD analysis disfavor the appearance of Sorafenib tosylate form I during the desolvation step to provide Sorafenib tosylate form III.

A preparation method of Sorafenib tosylate EtOH solvate from isolated and dried Sorafenib hemi-tosylate was successfully developed giving good yields (80-85%) without appearance of Sorafenib tosylate form I (monitoring by XRPD). The experimental part describes also this process.

The process of the present invention can be carried out at one temperature comprised between 10° C. and 40° C., being preferred a range of temperature comprised between 15° C. and 35° C., being more preferred between 20° C. and 30° C.

The process of the present invention can be conveniently carried out at room temperature.

No significant effect was observed in the experiments using a large amount of Sorafenib tosylate ethanol solvate seeding (e.g. 25% weight of seed).

According to a preferred embodiment of the invention, Sorafenib tosylate ethanol solvate can be prepared forming Sorafenib hemi-tosylate in situ from Sorafenib free base in EtOH 90-95% v/v. In other words, according to a preferred embodiment of the invention, the preparation of a suspension of Sorafenib hemi-tosylate in EtOH 90-95% v/v can be carried out in a one-pot process, starting from Sorafenib base, without the isolation of the compound Sorafenib hemi-tosylate of formula (II) or hydrates thereof.

Preparation of SRFB Hemitosylate in situ by slow addition (4 hours) of TsOH (1.2 eq) to a suspension of Sorafenib free base in EtOH 90% or 92% v/v (10 vol.) was successful.

According to a preferred embodiment of the invention, the step a) is carried out by addition of a solution of TsOH (1.2 eq.-2 vol.) in EtOH 92% v/v to a suspension of Sorafenib free base in EtOH 92% (8 vol.) (addition time 4 h).

According to a preferred embodiment of the invention, the step b) is carried out by addition of a solution of TsOH (1.3 eq.-2 vol.) in EtOH 92% v/v to a suspension of Sorafenib hemi-tosylate (addition time 4 h).

According to a more preferred embodiment of the invention:
the step a) is carried out by addition of a solution of TsOH (1.2 eq.-2 vol.) in EtOH 92% v/v to a suspension of Sorafenib free base in EtOH 92% (8 vol.) (addition time 4 h) and the step b) is carried out by addition of a solution of TsOH (1.3 eq.-2 vol.) in EtOH 92% v/v to a suspension of Sorafenib hemi-tosylate (addition time 4 h).

This preparation method afforded successfully Sorafenib tosylate ethanol solvate at 2 and 5 g scale, then Sorafenib hemi-tosylate formed in situ was stirred overnight before performing the EtOH solvate formation step: it remained stable.

According to a preferred embodiment of the invention, in the step b) a very slow addition (i.e. from 0.5 to 12 hours) of an EtOH 90-95% v/v solution containing a large excess of TsOH (2 eq.) over a suspension of Sorafenib hemi-tosylate in EtOH 90-95% v/v is preferred since it avoid the appearance of Sorafenib tosylate form I and also ensures a complete conversion.

According to a preferred embodiment of the process of the invention, Sorafenib hemi-tosylate of formula (II) employed in the step a) is prepared starting from Sorafenib base of formula (III):

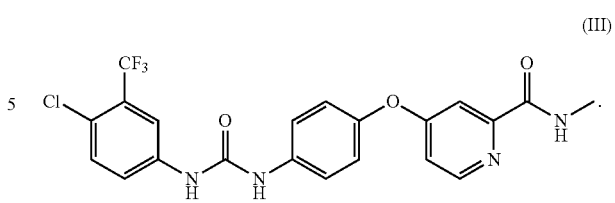

(III)

For the preparation of Sorafenib tosylate ethanol solvate starting from Sorafenib base instead of from Sorafenib hemitosylate, similar dilution, amount of water in EtOH, volumes of solvent, amount of TsOH, and addition rate of TsOH solution to that used for the conversion of Sorafenib hemi-tosylate can be used in order to prepare Sorafenib tosylate ethanol solvate directly from the Sorafenib free base. However, as the starting product is Sorafenib free base instead of Sorafenib hemi-tosylate, additional 0.5 eq. of TsOH have to be used.

The XRPD monitoring of this reaction indicated:
No appearance of Sorafenib tosylate form I during Sorafenib hemi-tosylate and Sorafenib tosylate ethanol solvate formation;
Complete formation of Sorafenib hemi-tosylate after the first three hours of TsOH addition.

Sorafenib tosylate ethanol solvate was obtained satisfactorily using ethanol 90% and 95% v/v without the appearance of Sorafenib tosylate form I. The proportion of water in ethanol seems not to affect the formation of Sorafenib hemi-tosylate. However, the increase of water proportion in ethanol causes a decrease in the conversion rate of Sorafenib hemi-tosylate intermediate into Sorafenib tosylate ethanol solvate:
with EtOH 94% v/v the conversion was complete before the end of the TsOH solution addition; and
with EtOH 91% v/v the conversion was completed 1 hour after the end of the addition. However, the slurrying was kept at RT overnight.

The effect of the dilution was studied.

The final volume of EtOH 92% v/v used in the preparation method is 12 vol. (8 vol. (initial)+4 vol. (addition 2.5 eq. TsOH). In order to not modify the addition rate of TsOH solution, this process was checked using different initial volume of EtOH 92% v/v: 6 and 10 vol.

In both cases, Sorafenib tosylate ethanol solvate was successfully obtained without appearance of Sorafenib tosylate form I. No significant change of conversion rate of Sorafenib hemi-tosylate into Sorafenib tosylate ethanol solvate was observed when 6 vol. or 10 vol. of EtOH 92% v/v was used as initial volume. This fact shows the robustness of the process expanding the safety margins of the corresponding parameter of dilution of the reaction.

Effect of Stirring Rate.

A slow stirring can involve the formation of non-homogenous mixture, especially local concentration of TsOH during the addition, that could lead to the formation of Sorafenib tosylate form I. In order to check its effect, some experiments were performed with a slow stirring rate.

Even with a slow stirring rate, when EtOH 90-95% v/v was used, Sorafenib tosylate Ethanol solvate was obtained without appearance of Sorafenib form I. However, the rate of conversion of Sorafinib hemi-tosylate into Sorafenib tosylate ethanol solvate decreased, and two extra hours of stirring at RT was necessary to ensure complete conversion.

According to a preferred embodiment of the process of the present invention, in the step d) the product can be washed one or more times with absolute EtOH, since it provides a more stable product towards the conversion to Sorafenib tosylate form I.

Another aspect of the present invention is a process for the preparation of Sorafenib tosylate form III of formula (I):

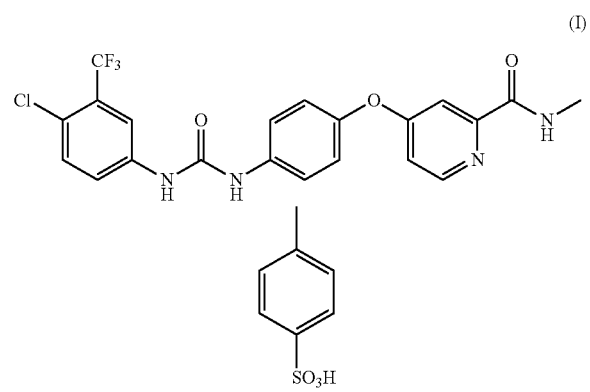

comprising the following steps:
1) preparing Sorafenib tosylate ethanol solvate of formula (I-EtOH) according to the process above described,
2) optionally,
    a) suspending isolated Sorafenib tosylate ethanol solvate of formula (I-EtOH) in ethanol, and
    b) stirring the suspension for a time comprised between 1 and 72 hours and then isolating the product of formula (I-EtOH),
3) heating under vacuum Sorafenib tosylate ethanol solvate of formula (I-EtOH) as obtained in the step 1 or step 2.

According to a preferred embodiment, the step 3) is carried out at temperature from 95° C. to 105° C.

The step 3), also named desolvation step, for preparing Sorafenib tosylate form III have to be carried out at temperature higher than 80-85° C. because for large amounts of Sorafenib tosylate ethanol solvate operating into said range of temperature requires too much time to complete the conversion to Form III.

To the other side higher temperature, promotes the conversion of Form III towards to Form I.

At 110° C. under vacuum, the conversion is complete after some hours but form I appeared before the end of the conversion in almost all the cases.

At 100° C. under vacuum, the conversion is complete after one night.

At 80° C. under vacuum, the conversion was complete at very low scale after one night, but a higher temperature was necessary at higher scale.

Stability studies of the free Sorafenib tosylate form III were already performed. These studies indicate that form III remained stable 3 months under accelerated conditions of ICH guideline (40° C.-70% RH) and less than 7 months at RT under 94% RH, while it remained stable at least 7 month at RT under 60% RH.

Finally, Sorafenib tosylate ethanol solvate was dried at 100° C. under vacuum (4 mbar) until desolvation was completed (24 hours approximately for 5 g).

It has been found that the temperature to perform the desolvation step is between 95° C. and 105° C., being 100° C. the best temperature.

A batch of Sorafenib tosylate ethanol solvate that previously failed to afford Sorafenib tosylate form III not contaminated with Sorafenib tosylate form I was slurred in absolute EtOH.

In particular, Sorafenib tosylate ethanol solvate was stirred overnight in 10 vol. of absolute ethanol at RT before filtering with a sinter funnel (porosity no 3) and washing with absolute ethanol (2×2 vol.). Then the resulting white solid was dried under high vacuum at room temperature for 15 h.

A part of this solid (1.5 g) was desolvated at 100° C. under vacuum (4 mbar). This desolvation was monitored by XRPD and softly milled each hour. After 6 hours Sorafenib tosylate form III was obtained and Sorafenib tosylate form I was not observed during all the process.

This successful result seems not due to a decrease of the residual amount of water caused by the slurrying with absolute EtOH because Karl Fischer analysis of a sample of Sorafenib tosylate ethanol solvate before and after slurrying in absolute EtOH indicated similar amount of water (0.6% $H_2O$, 0.23 equivalents of $H_2O$) but it seems due to the complete conversion of any possible microseeding of Sorafenib tosylate form I into Sorafenib tosylate ethanol solvate.

In other words, it has been discovered that suspending isolated Sorafenib tosylate ethanol solvate of formula (I-EtOH) in ethanol, and stirring the suspension for a time comprised between 1 and 72 hours, and then isolating the product of formula (I-EtOH), it is possible to prepare Sorafenib tosylate ethanol solvate with increased stability towards the conversion to Sorafenib tosylate form I, and therefore, which provides Sorafenib tosylate form III without any trace of Sorafenib tosylate form I.

Thus, another aspect of the present invention is a process for the preparation of Sorafenib tosylate form III of formula (I):

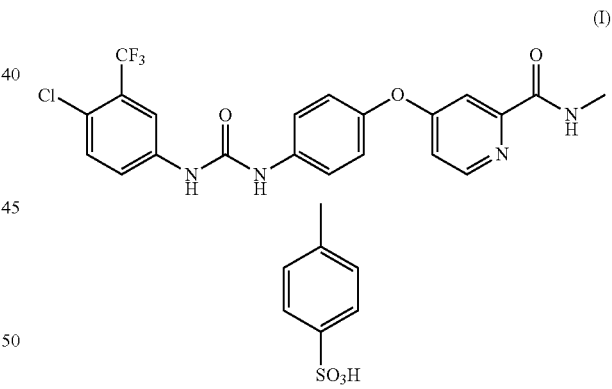

comprising the following steps:
a) suspending isolated Sorafenib tosylate ethanol solvate of formula (I-EtOH):

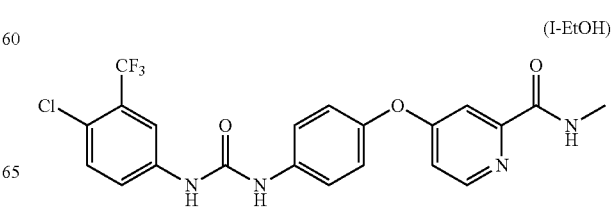

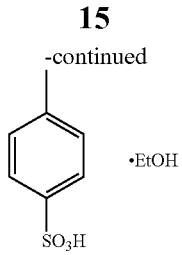

in ethanol,
b) stirring the suspension for a time comprised between 1 and 72 hours and isolating the product of formula (I-EtOH),
c) heating under vacuum the Sorafenib tosylate ethanol solvate of formula (I-EtOH) as obtained in the step b).

According to a preferred embodiment the above process, the step c) is carried out at one temperature comprised between 95-105° C.

According to a preferred embodiment the above process can be carried out as follow:
a) suspending isolated Sorafenib tosylate ethanol solvate in 10 volumes of ethanol,
b) stirring overnight at RT then the suspension is filtered and the solid is washed with absolute EtOH (2×2 vol.), thus isolating Sorafenib tosylate ethanol solvate,
c) drying the resulting solid under high vacuum at 100° C. for 15 h.

DSC Monitoring.

It was found that it should be possible to monitor the conversion of the different preparation steps of Sorafenib tosylate ethanol solvate, if the samples are filtered, washed twice with the reaction solvent and dried under vacuum at RT before DSC analysis.

The excess of TsOH used in the steps of formation of Sorafenib hemi-tosylate and Sorafenib tosylate ethanol solvate makes the interpretation almost impossible. Therefore, this excess of TsOH should be eliminated.

Using the preparation of samples described above it was observed that:
For Sorafenib hemi-tosylate formation step it is possible to monitor the disappearance of Sorafenib free base and appearance of Sorafenib hemi-tosylate.
For Sorafenib tosylate ethanol solvate formation step:
In spite of the superposition of ethanol desolvation/Sorafenib tosylate Form III formation and dehydration/fusion Sorafenib hemi-tosylate, it is possible to observe the disappearance of Sorafenib hemi-tosylate by DSC for the profile modification of this thermal event. Furthermore, melting points of Form III increase with the purity of medium to reach the reference melting point when the conversion is complete.
However, Form III appeared only when the Sorafenib tosylate ethanol solvate is the major crystalline phase in the medium. Sorafenib tosylate form III coming from the desolvation process seems to be dissolved in the melt of Sorafenib hemi-tosylate.
It was also possible to monitor the appearance and disappearance of Sorafenib tosylate form I at the end of TsOH addition.
For ethanol desolvation step it is possible to monitor the disappearance of Sorafenib tosylate ethanol solvate.
However it is not possible to observe contamination of Sorafenib tosylate form III with form I because form III recrystallized to form I during DSC analysis.

A preparation method of Sorafenib tosylate ethanol solvate directly from Sorafenib free base was developed with success affording good yields (80-90%) without appearance of Sorafenib tosylate form I (monitoring by XRPD). The experimental part describes the actual most robust process and it was scaled up to 25 g.

Sorafenib tosylate form III was successfully obtained by thermal desolvation of Sorafenib tosylate ethanol solvate obtained from Sorafenib directly at 100° C. under vacuum (4 mbar) avoiding the appearance of the Sorafenib tosylate form I.

The desolvation process from Sorafenib tosylate ethanol solvate affords Sorafenib tosylate form III with a slightly lower crystallinity than Sorafenib tosylate form III obtained from the Sorafenib tosylate methanol solvate. This lower crystallinity seems not to be due to the higher temperature of desolvation because no difference of crystallinity was observed at 90° C., 100° C. and 110° C. The ethanol molecule, a little bigger than methanol, could cause the formation of smaller crystals of Sorafenib tosylate form III during the desolvation step leading to a solid with a lower crystallinity.

As the stability study of Sorafenib tosylate form III was performed with Sorafenib tosylate form III obtained from Sorafenib tosylate methanol solvate, only a minor difference in behavior could be possible with this new solid.

In conclusion it has been found a preparation method of Sorafenib tosylate Form III without contamination of Form I and stable towards the conversion to form I, passing through the intermediate from desolvation of Sorafenib tosylate ethanol solvate prepared from Sorafenib hemi-tosylate.

According to another aspect of the invention, Sorafenib hemi-tosylate of formula II) or hydrates thereof:

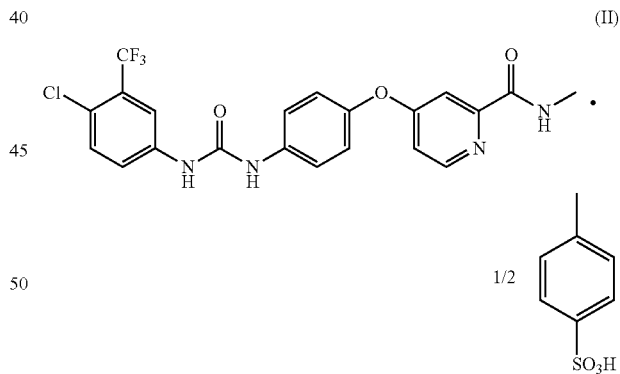

can be used for preparing Sorafenib tosylate ethanol solvate of formula (I-EtOH):

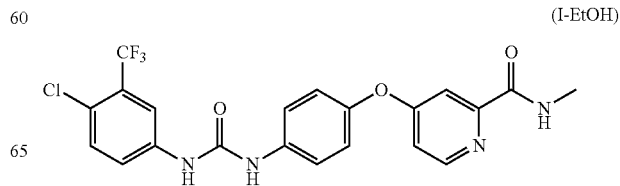

or for preparing Sorafenib tosylate form III of formula (I):

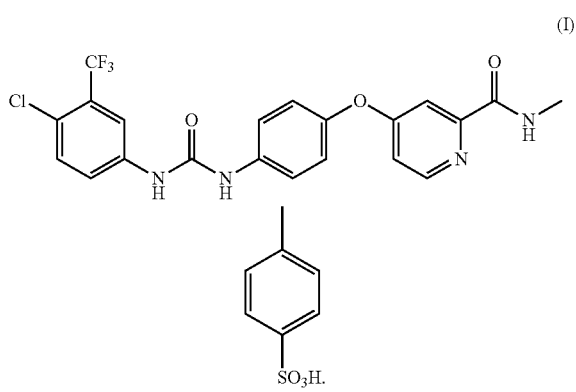

According to a preferred embodiment, Sorafenib hemi-tosylate or hydrates thereof is suspended in ethanol 90-95% v/v for preparing Sorafenib tosylate ethanol solvate or Sorafenib tosylate form III.

Different methods of Sorafenib hemi-tosylate preparation were described in the application WO2009/092070 starting from Sorafenib base or from Sorafenib tosylate form III. These methods were reproduced in laboratory affording Sorafenib tosylate form I or Sorafenib hemi-tosylate contaminated with Sorafenib tosylate form I.

Therefore, a new method for the preparation of Sorafenib hemi-tosylate monohydrate, without the appearance of Sorafenib tosylate form I, was developed.

The following method is an alternative process for the preparation of Sorafenib hemi-tosylate, alternative to the process starting from Sorafenib base in ethanol 90-95% v/v as above described.

Both the methods allow the preparation of the starting material Sorafenib hemi-tosylate without the appearance of Sorafenib tosylate form I, thus allowing the preparation of Sorafenib tosylate ethanol solvate or Sorafenib tosylate form III stable toward the conversion to form I, according to the process of the present invention.

Sorafenib hemi-tosylate of formula (II) or hydrates thereof, i.e. the starting material for preparing Sorafenib tosylate ethanol solvate or Sorafenib tosylate form III according to the process of the present invention, thus can be prepared according to the following alternative process:
by addition of from 0.55 to 0.8 mol. eq. of paratoluensulfonic acid or hydrates thereof solubilized in a specific amount of water to a suspension of Sorafenib base of formula (III):

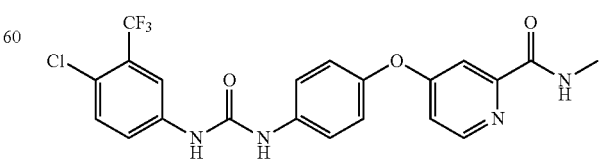

in 1-propanol.

It was indeed found that adding from 0.55 to 0.8 mol. eq. of paratoluensulfonic acid or hydrates thereof solubilized in a specific amount of water, to a suspension of Sorafenib base in 1-propanol affords Sorafenib hemi-tosylate as a crystalline pure form with good yield (92%), without the appearance of Sorafenib tosylate form I, wherein said specific amount of water is from 5% to 20% v/v compared with the volume of 1-propanol. The amount of 0.55 to 0.8 mol. eq. of paratoluensulfonic acid or hydrates is the essential feature to achieve said result, i.e. to avoid the appearance of Sorafenib tosylate form (I).

According to a preferred embodiment, the specific amount of water is 10% v/v compared to the volume of 1-propanol.

According to another preferred embodiment, the amount of 0.7 mol. eq. of paratoluensulfonic acid or hydrates thereof is preferred.

According to a preferred embodiment, Sorafenib hemitosylate monohydrate is prepared.

According to a preferred embodiment, Sorafenib hemitosylate is prepared from Sorafenib base using the method described in example 1.

This process was scaled up to 25 g affording Sorafenib hemi-tosylate monohydrate as a pure form with excellent yield (93%)).

Sorafenib hemi-tosylate or hydrates thereof prepared according this alternative method is suitable as starting material in a process for the preparation of Sorafenib tosylate ethanol solvate or Sorafenib tosylate form III stable toward the conversion to form I, according to the process of the present invention.

Thus, another aspect of the present invention is a process for preparing Sorafenib tosylate ethanol solvate or Sorafenib tosylate form III, wherein the step a) the provision of a suspension of Sorafenib hemi-tosylate of formula (II) or hydrates thereof is carried out by suspending in ethanol 90-95% v/v Sorafenib hemi-tosylate prepared by addition of from 0.55 to 0.8 mol. eq. of paratoluensulfonic acid or hydrates thereof solubilized in amount of water from 5% to 20% v/v compared to the volume of 1-propanol, to a suspension of Sorafenib base of formula (III):

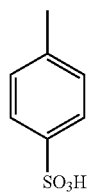

in 1-propanol.

Thus, for example, if Sorafenib base is suspended in 10 volumes of 1-propanol (or n-propanol), then TsOH or hydrates thereof have to be solubilized in from 0.5 to 2.0 volumes of water.

EXPERIMENTAL SECTION

The starting material Sorafenib free base of formula (III) was prepared according to the teachings of EP1140840 or WO2006034796.

TsOH means paratoluensulfonic acid, of SRFB means Sorafenib and SRFB.TsOH means Sorafenib tosylate. EtOH=ethanol.

The polymorphic forms Sorafenib tosylate form I, form III and ethanol solvate of the present invention are the same of those described in EP1797038 and WO2009/092070 whose description are enclosed here by reference.

Example 1: Synthesis and Characterization of Sorafenib Hemi-Tosylate Monohydrate of Formula (II)

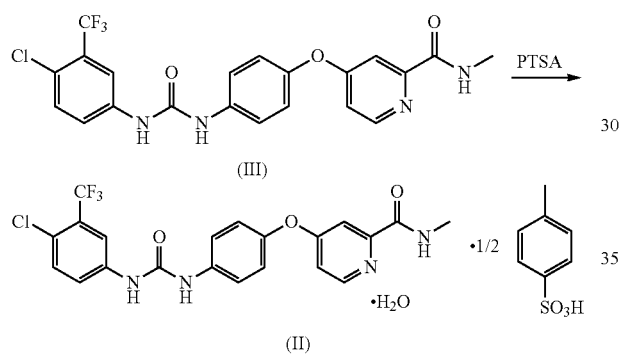

A suspension of SRFB free base (1 g, 2.15 mmol) in 1-propanol (13 mL) was heated to 50° C. in a 100 mL flask equipped with mechanical stirring. The resulting slightly turbid mixture was cooled to RT before adding dropwise, in four portions during 30 minutes, a solution of pTsOH.H$_2$O (286 mg, 1.50 mmol, 0.7 eq.) in water (1.3 mL). The resulting suspension was seeded with SRFB Hemitosylate and was allowed to crystallize 4 h at RT and 2 h at 0-5° C. The solid was filtered off with a sinter funnel no 3, washed with cold 1-propanol/water 1.8:0.2 (2×2 mL) and dried under high vacuum at RT for 15 h affording pure Sorafenib hemi-tosylate monohydrate as a slightly yellow solid (1.09 g, 92%).

This experiment has been repeated on scale 100 g affording crystalline pure Sorafenib hemi-tosylate monohydrate with 92% of molar yield. In this case the seeding has been not used and the addition has been carried out in continuous over 30 min.

Characterization of Sorafenib-Hemitosylate Monohydrate.

Sorafenib hemi-tosylate called Form A prepared in WO2009/092070 was only partially characterized: XRPD and solid state $^{13}$C-NMR.

Sorafenib hemitosylate prepared according to experiment 1 was characterized by $^1$H-NMR, XRPD, DSC, TGA, Karl Fischer and IR.

$^1$H-NMR

Proton nuclear magnetic resonance analyses were recorded in deuterated dimethyl sulfoxide (DMSO-d$_6$) in a Varian Mercury 400 spectrometer, equipped with a broad-band probe ATB 1H/19F/X of 5 mm. Spectra were acquired dissolving 5-10 mg of sample in 0.6 mL of deuterated solvent.

$^1$H-NMR (DMSO-d$_6$, 400 MHz): δ (ppm)=9.25 (s, 2H); 9.04 (s, 2H); 8.81 (d, J=4.0 Hz, 2H); 8.52 (d, J=6.0 Hz, 2H); 8.12 (d, J=2.4 Hz, 2H); 7.68-7.58 (m, 8H); 7.49 (d, J=8.0 Hz, 2H); 7.43 (s, 2H); 7.20-7.16 (m, 6H); 7.12 (d, J=8.4 Hz, 2H); 2.79 (d, J=8.4 Hz, 6H); 2.29 (s, 3H).

1H-NMR analysis shows the presence of 0.5 eq. of TsOH which confirms the formation of Sorafenib hemi-tosylate.

XRPD

XRPD analysis was performed using a PANalytical X'Pert diffractometer with Cu Kα radiation in Bragg-Brentano geometry. The system is equipped with a monodimensional, real time multiple strip detector. The diffractogram was recorded from 3° to 40° (2θ) at a scan rate of 0.0205° per second. The XRPD diffractogram matches with the diffractogram of Sorafenib hemi-tosylate described in WO2009/092070. List of selected peaks (only peaks with relative intensity greater than or equal to 5% are indicated):

| Pos. [°2Th.] | Rel. Int. [%] |
|---|---|
| 5.6 | 8 |
| 6.6 | 14 |
| 8.0 | 6 |
| 9.0 | 56 |
| 9.6 | 46 |
| 9.9 | 30 |
| 10.9 | 17 |
| 11.2 | 13 |
| 11.3 | 11 |
| 12.5 | 5 |
| 12.7 | 5 |
| 13.4 | 100 |
| 13.8 | 70 |
| 14.0 | 86 |
| 14.5 | 15 |
| 15.1 | 9 |
| 15.7 | 31 |
| 16.1 | 14 |
| 16.5 | 44 |
| 16.7 | 44 |
| 17.0 | 47 |
| 17.2 | 68 |
| 18.4 | 46 |
| 18.9 | 22 |
| 19.3 | 34 |
| 19.8 | 52 |
| 19.9 | 19 |
| 20.4 | 74 |
| 20.7 | 64 |
| 21.0 | 8 |
| 21.3 | 32 |
| 21.5 | 42 |
| 22.3 | 13 |
| 22.8 | 39 |
| 22.9 | 25 |
| 23.3 | 25 |
| 23.6 | 46 |
| 23.7 | 58 |
| 24.1 | 40 |
| 24.6 | 46 |
| 24.9 | 73 |
| 25.5 | 26 |
| 25.8 | 37 |
| 26.1 | 16 |
| 26.4 | 5 |
| 27.1 | 70 |
| 27.4 | 46 |
| 28.3 | 26 |

-continued

| Pos. [°2Th.] | Rel. Int. [%] |
|---|---|
| 28.6 | 6 |
| 29.1 | 10 |
| 29.8 | 12 |
| 30.3 | 6 |
| 31.1 | 10 |
| 32.6 | 14 |
| 33.5 | 9 |
| 34.0 | 15 |
| 34.8 | 10 |
| 36.3 | 5 |
| 36.7 | 9 |
| 38.8 | 6 |

The XRPD pattern matches with the XRPD Sorafenib hemi-tosylate Form A pattern described in the patent WO2009/092070.

Karl-Fischer

Karl-Fischer analyses were recorded with a Metrohm 787 KF Trinito. The product was dissolved in MeOH. Two samples were analyzed using the following reactants: Hydranal-Composite 5 (Riedel de Haën Ref. 34805), Hydranal Methanol Rapid (Riedel de Haën Ref. 37817) and Hydranal Water Standard 1.0 (Riedel de Haën Ref. 34828 used to calculate the factor).

The water content of Sorafenib hemi-tosylate is 5.0%. Further KF analysis performed with the same sample dried at 80° C. under vacuum overnight gave a water content of 3.9% (corresponding to 1.25 mol equivalent water). This confirms that Sorafenib hemi-tosylate is a monohydrate.

DSC

DSC analysis was recorded with a Mettler DSC822 e. A sample of 2.2330 mg was weighed into a 40 μL aluminium crucible with a pinhole lid and was heated, under nitrogen (50 mL/min), at 10° C./min from 30 to 300° C. Sorafenib hemi-tosylate is characterized by an endothermic sharp peak corresponding to the melting point having a maximum at 140.22° C. (fusion enthalpy −74.54 J/g), measured by DSC analysis (10° C./min). Another endothermic peak was also observed just before the melting point of SRFB Hemitosylate with an onset at 88.81° C. (fusion enthalpy −39.25 J/g). This thermal event could come from a partial dehydration of SRFB hemi-tosylate monohydrate.

After the fusion of Sorafenib hemi-tosylate, an exothermic peak corresponding to the crystallization of another crystalline form with a maximum at 166.04° C. (crystallization enthalpy 21.55 J/g) was observed. Then another endothermic peak corresponding to the fusion of this new crystalline form was observed with an onset at 179.44° C. (fusion enthalpy −12.78° C.). This new form could be another Sorafenib hemi-tosylate or a Sorafenib tosylate crystalline form.

TGA

Thermogravimetric analysis was recorded in a thermogravimetric analyzer Mettler TGA/SDTA851e.

A sample of 6.0202 mg was weighed into a 70 μL alumina crucible with a pinhole lid and was heated at 10° C./min from 30 to 300° C., under nitrogen (50 mL/min).

The TG analysis of Sorafenib hemi-tosylate shows a weight loss between 53.96 and 165.48° C. corresponding to the loss of ca. one water molecule (2.7%, calc. 3.1%; see FIG. 5) confirming that Sorafenib hemi-tosylate is a monohydrate by Karl-Fischer analysis (see section above—water content 3.9%). However it can be observed that the water was lost in two stages of ca. 0.5 water molecule.

Superposition of DSC and TGA indicates that the first loss of ca. 0.5 water molecule corresponds to the thermal event of dehydration and the second loss of ca. 0.5 water molecule corresponds to the melting of SRFB hemi-tosylate Therefore, it seems that the second thermal event is the melting of a new crystalline Sorafenib hemitosylate hemihydrate.

However, it was not possible to identify this new crystalline form by XRPD after several attempts of drying at 105° C. and 115° C. under vacuum followed by a fast XRPD analysis: in all the cases a XRPD pattern identical to the previously known SRFB hemi-tosylate monohydrate was observed. Therefore, this SRFB hemi-tosylate hemihydrate could be isostructural to SRFB hemi-tosylate monohydrate or SRFB hemi-tosylate hemihydrate could revert so fast to SRFB hemi-tosylate monohydrate under laboratory atmosphere that it was not possible to analyse.

IR

IR analysis was performed using a Nexus thermos Nicolet, AES0100443. IR spectrum, ν cm$^{-1}$ KBr, thin film): 3350, 3297, 3093, 2936, 1720, 1681, 1661, 1650, 1598, 1563, 1552, 1537, 1504, 1480, 1462, 1421, 1331, 1307, 1284, 1254, 1227, 1177, 1123, 1030, 1005, 923, 859, 839, 682, 661, 572, 554.

Stability Study

Four different humidity/temperature conditions were selected for this study:

Humidity (60% RH) at room temperature,
High humidity (94% RH) at room temperature,
Accelerated conditions of ICH guidelines (40° C.-70% RH),
80° C. under vacuum.

No crystalline changes were detected by XRPD after 119 days at 60 or 94% RH at room temperature or at 70% RH at 40° C. Nevertheless, after 88 days at 80° C. under vacuum traces of Sorafenib free base were observed by XRPD analysis.

Conclusions

Karl-Fischer and DSC/TGA analyses confirmed that Sorafenib hemi-tosylate is a monohydrate (water content 3.9% for KF and 2.7% for TGA—3.1% calc. for a monohydrate). This form was previously characterized in WO2009/092070 but, as Karl-Fischer and TGA were not performed, the presence of water in this crystalline form was not mentioned. An update of the stability studies indicates that Sorafenib hemi-tosylate remained stable at 60% or 94% RH at room temperature and at 70% RH at 40° C. for at least four months. However, at 80° C. under vacuum, traces of SORAFENIB free base were detected after almost three months.

Example 2: DSC Study for Monitoring the Preparation of Sorafenib Tosylate Ethanol Solvate In a first stage DSC analysis of Sorafenib hemy-tosylate monohydrate prepared from Sorafenib free base or from Sorafenib tosylate form I were performed in order to help DSC interpretations.

All the DSC analysis were performed in aluminum crucible at 10° K/min under nitrogen (50 mL/min).

it was found that it should be possible to monitor the conversion of the different preparation steps of EtOH solvate, if the samples were filtered, washed twice with EtOH 92% v/v and dried under vacuum at RT before DSC analysis.

The excess of TsOH used in the steps of formation of Sorafenib hemi-tosylate and Sorafenib tosylate ethanol solvate makes the interpretation almost impossible. Therefore this excess of TsOH must be eliminated.

Figure 2:
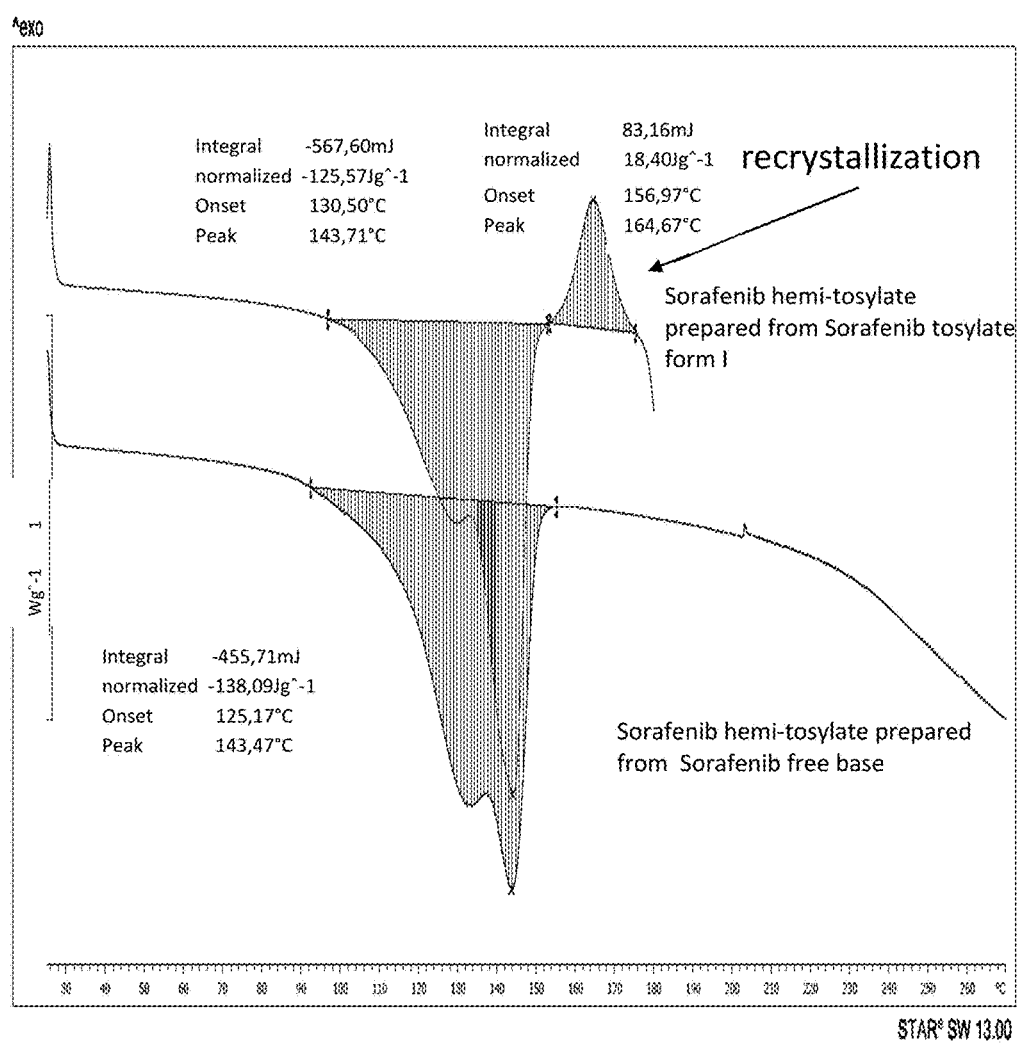
FIG. 2 shows the DSC curves of Sorafenib hemi-tosylate monohydrate prepared starting from Sorafenib base or starting from Sorafenib tosylate form I.

The DSC analysis is different according to the Sorafenib hemi-tosylate preparation method (see FIG. 2).

In particular, when the Sorafenib hemi-tosylate is prepared from the Sorafenib free base (crystallization n-PrOH/water), new thermic events are not observed after the fusion. Viceversa, when SRFB hemitosylate was prepared by slurrying in water from Sorafenib tosylate form I a recrystallization was observed after the melt process (peak at about 165° C.).

This thermic event could come from microseedings of SRFB.TsOH form I still presents into Sorafenib hemitosylate prepare from SRFB.TsOH form I.

In order to check this hypothesis a DSC analysis of a sample of SRFB hemitosylate (prepared from Sorafenib base) contaminated by addition of a small amount of SRFB.TsOH form I was performed.

The same thermic event was observed for both samples.

Therefore the presence of microseeds of SRFB.TsOH Form I into Sorafenib hemi-tosylate generates the thermic event of recrystallization after the fusion of SRFB Hemitosylate (peak at about 165° C.).

The DSC curve of FIG. 2, in particular the presence or absence of the peak at 165° C., is diagnostic of the presence of microseedings of Sorafenib tosylate form I into Sorafenib hemi-tosylate monohydrate.

FIG. 3 shows the preparation of SRFB.TsOH EtOH solvate by slow addition of a solution of TsOH in EtOH abs (7 h, 1.3 eq.) over a slurrying of SRFB hemitosylate in EtOH 88%.

Appearance of Sorafenib tosylate Form I was observed at the end of the addition by XRPD and DSC. An exothermic peak of crystallization of Form I similar to the peak of crystallization observed when hemitosylate was contaminated with Form I, was detected.

After the appearance it is possible to observed the conversion of this Form I into EtOH solvate with time (not present after a slurrying overnight in EtOH 93%)

FIG. 4 shows the preparation of SRFB.TsOH EtOH solvate by slow addition of a TsOH solution in EtOH 92% (2 eq.-8 h) over a suspension of SRFB hemitosylate in EtOH 92%

It is possible to observe the disappearance of SRFB Hemitosylate by DSC.

Operating the conversion of SRFB hemitosylate into Sorafenib tosylate Ethanol solvate in Ethanol 92% v/v these is not appearance of the transient Sorafenib tosylate form I, as instead in the case showed by FIG. 3.

Example 3: Preparation of Sorafenib Tosylate Ethanol Solvate of Formula (I-EtOH) from Sorafenib Hemi-Tosylate Monohydrate of Formula (II)

Scheme of Synthesis:

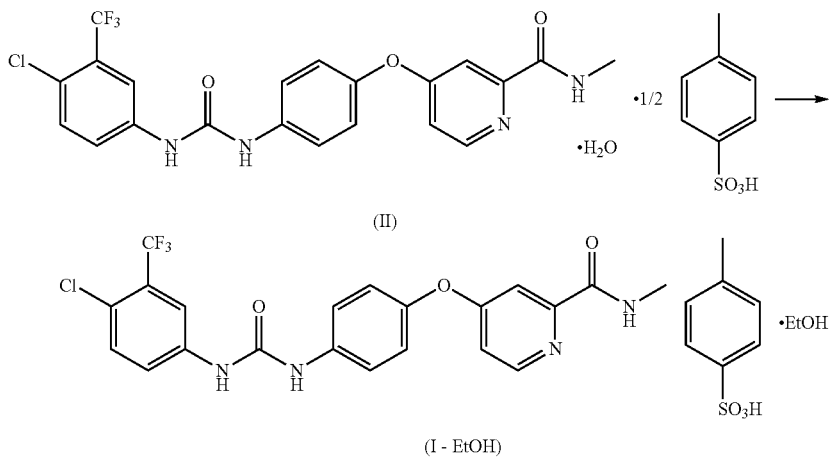

To a 250 mL three necked flask equipped with mechanical stirring containing SRFB hemi-tosylate monohydrate (5 g, 8.79 mmol) in EtOH (94% v/v, 40 mL) at RT, was added dropwise a solution of TsOH.H2O (1.337 g, 7.03 mmol, 0.8 eq.) in EtOH 94% (7.5 mL) during 30 min before stirring for 2 h at RT (the suspension was seeded with SRFB.TsOH EtOH solvate at the beginning and end of the addition). A solution of TsOH.H$_2$O (0.334 g, 1.76 mmol, 0.2 eq.) in EtOH (94% v/v, 1.67 mL) was added dropwise to the suspension before stirring for 2 h at RT. Finally, a solution of TsOH.H$_2$O (0.167 g, 0.88 mmol, 0.1 eq.) in EtOH (94% v/v, 0.83 mL) was added dropwise to the suspension before stirring for 2 h at RT.

The solid was filtered off with a sinter funnel no 3, washed with EtOH (94% v/v, 2×10 mL) and dried under high vacuum at RT for 15 h affording pure SRFB.TsOH EtOH solvate (5.08 g, 84%) as a beige/off-white solid.

The color of the suspension is an indicator of the conversion. As SRFB hemitosylate is a yellowish solid, the initial suspension is yellow. This yellow color converted with time into a beige color indicating advanced conversion.

The crystals of SRFB.TsOH EtOH solvate obtained using mechanical stirring are bigger than the crystals obtained with magnetic stirring affording a beige/off-white color instead of white.

The reaction was monitored by XRPD. A wet sample of the suspension was analyzed at the end of each addition and then after each hour. Sorafenib tosylate form I was not observed during the process.

The final product analyzed by XRPD under very sensitive conditions (32 min) indicated a pure Sorafenib tosylate ethanol solvate crystal form.

Example 4: Preparation of Sorafenib Tosylate Ethanol Solvate of Formula (I-EtOH) from Sorafenib Base of Formula (III) Via In Situ Preparation of Sorafenib Hemi-Tosylate Monohydrate of Formula (II)

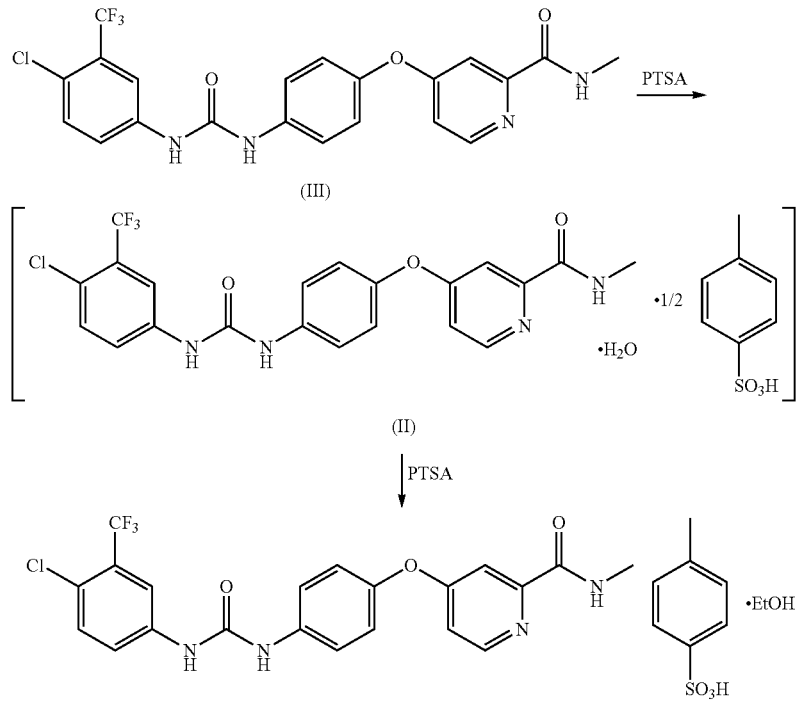

To a 10 mL flask equipped with magnetic stirring containing SRFB (200 mg, 0.43 mmol) in EtOH (90% v/v, 2.5 mL) at reflux, was added dropwise a hot solution of TsOH.H₂O (98 mg, 0.52 mmol, 1.2 eq.) in EtOH (90% v/v, 0.6 mL) (partial dilution was observed). The resulting suspension was seeded with SRFB hemi-tosylate monohydrate and cooled slowly to RT (the seeding was repeated each 10 min during the cooling). A solution of TsOH.H₂O (24.7 mg, 0.13 mmol, 0.3 eq.) in abs. EtOH (1 mL) was then added dropwise at RT (addition time 60 min). Abs. EtOH (4.4 mL) was added dropwise and during the addition the suspension was seeded with SRFB EtOH solvate. The resulting suspension was stirred 3 h at RT. The solid was filtered off with a sinter funnel no 3, washed with EtOH (96% v/v, 2×0.4 mL) and dried under high vacuum at RT for 15 h affording pure SRFB EtOH solvate (230 mg, 78%) as a white solid.

Example 5: Better Preparation of Sorafenib Tosylate Ethanol Solvate of Formula (I-EtOH) from Sorafenib Base of Formula (III) Via In Situ Preparation of Sorafenib Hemi-Tosylate Monohydrate of Formula (II)

Scheme of Synthesis:

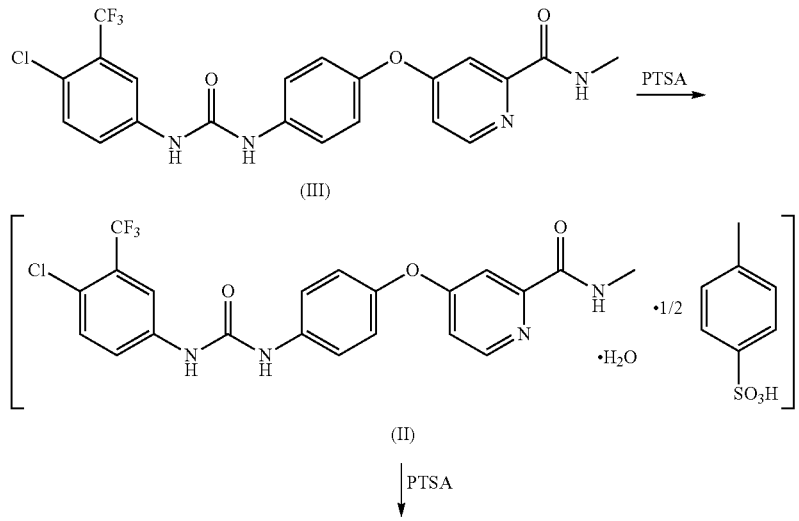

-continued

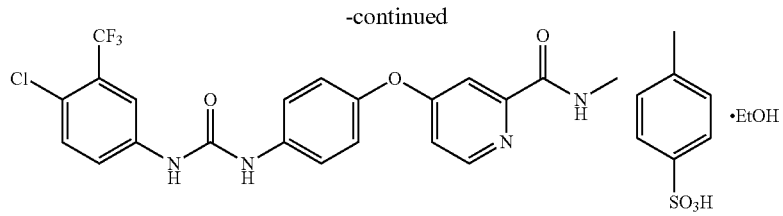

Sorafenib free base of formula (III) (5 g, 10.75 mmol) is suspended in EtOH 92% v/v (40 mL) in a 3-necked 250 ml round bottom flask, equipped with mechanical stirring. To the stirred suspension, a solution of TsOH.H$_2$O (5.115 g, 26.89 mmol, 2.5 eq.) in EtOH 92% (20 mL) is added dropwise at RT (over an addition time of 8 h via an automatic syringe pump, approx. addition rate 0.042 mL/min).

During the first 4 hours of the addition, the resulting suspension is seeded every hour with SRFB Hemitosylate (starting when the addition begins, 4 seeding take place).

During the remaining 4 h of the addition, the resulting suspension is seeded every hour with SRFB.TsOH EtOH solvate (therefore, starting 4 h after the addition begins, 4 seeding take place).

Once the addition is completed, the suspension is stirred at RT for another hour.

The resulting suspension is filtered through a sinter funnel (porosity no 3), the filtrated solid is washed with EtOH 92% v/v (2×10 mL) and dried under high vacuum at room temperature for 15 h to afford pure SRFB.TsOH EtOH solvate (6.38 g, 87%) as a beige/off-white solid.

At 2 g scale, a complete conversion is observed at the end of the addition. However, at 5 g scale at least 1 hour extra is necessary to obtain this complete conversion.

Alternative Embodiment of Example 5

Sorafenib tosylate ethanol solvate was also successfully obtained at 5 g scale in the same conditions but adding TsOH in two steps:

Step 1 (SRFB hemi-tosylate formation): 1.2 eq of TsOH.H$_2$O was added in 10 mL of EtOH 92% v/v during 4 h and after the addition, the resulting suspension was stirred at RT for another 15 h. It was observed that the SRFB Hemitosylate formed during the first part of the addition (step 1) remained stable in the mixture even after an additional overnight stirring at RT (SRFB.TsOH Form I was not observed).

Step 2 (SRFB.TsOH EtOH solvate formation): a solution of 1.3 eq of TsOH.H2O in 10 mL of EtOH 92% v/v was added to the previous resulting mixture during a period of 4 h and the resulting mixture was stirred for another hour at RT affording pure SRFB.TsOH EtOH solvate in 86% yield.

SRFB.TsOH EtOH solvate was also successfully obtained with EtOH 94% v/v at 2 g scale (2.63 g, 89% yield). In this case, the conversion was complete before the end of the addition (lower proportion of water increases the conversion rate). However the addition was maintained as planned: it was observed that SRFB.TsOH EtOH solvate remained stable even in presence of a large excess of TsOH.

The RT of our laboratory oscillates between 20° C. and 24° C. (humidity ranges 40-50%).

Preparation of 100 mL of EtOH 92% v/v: 92 mL of EtOH abs.+8 mL of deionized water.

EtOH abs (PANREAC, ref.: 141086.1214):
  EtOH: 99.5%
  H2O: 0.5% (Karl Fischer analysis indicates 0.025%)
Water deionized technical grade (PANREAC, ref.: 212236.0716):
  pH: 7.2 (measured experimentally)

The reactions were monitored every hour by XRPD. The suspension samples were filtered and washed with EtOH 92% v/v before analyzing the resulting wet solid by XRPD. SRFB.TsOH Form I was not observed during all the process. The final product analyzed by XRPD using very sensitive conditions (32 min) indicated a pure SRFB.TsOH EtOH solvate crystal form. Simultaneously, it was found that it should be possible to monitor the conversion of the two in situ preparation steps by DSC analysis if the samples were filtered, washed with EtOH 92% v/v and dried under vacuum at RT.

The Colour of the Suspension is an Indicator of the Conversion:

The initial light brown suspension of the SRFB free base in EtOH 92% v/v converted into a yellow suspension corresponding to Sorafenib hemi-tosylate (complete dissolution was not observed).

Then this yellow suspension converted with time into a beige colour indicating advanced conversion.

Example 6: Preparation of Sorafenib Tosylate Form III from Sorafenib Base of Formula (III) Through Sorafenib Hemi-Tosylate Monohydrate (Not-Isolated) and Sorafenib Tosylate Ethanol Solvate Scheme of Synthesis:

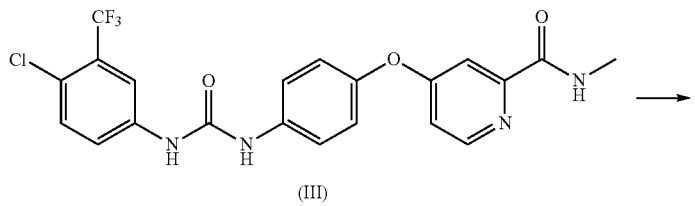

(III)

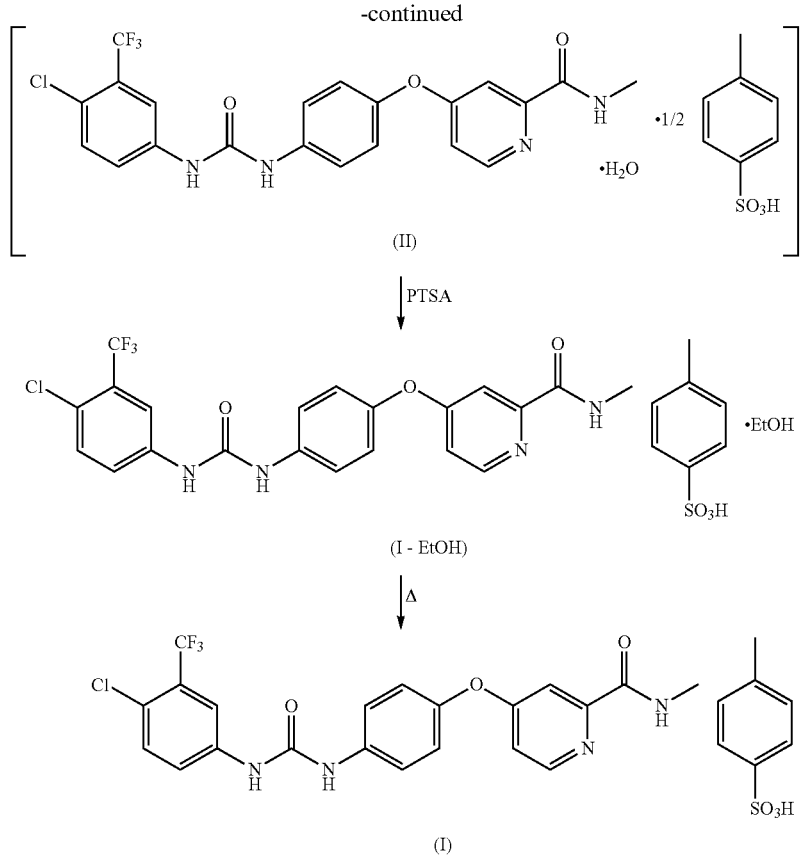

Sorafenib free base of formula (III) (25 g, 53.78 mmol) is suspended in EtOH 91% v/v (200 mL) in a 3-necked 500 ml round-bottomed flask, equipped with mechanical stirring. To the stirred suspension, a solution of paratoluesulfonic acid monohydrate (25.57 g, 134.46 mmol, 2.5 eq.) in EtOH 91% (100 mL) is added dropwise at RT (over an addition time of 8 h via an automatic syringe pump, approx. addition rate 0.21 mL/min).

During the first 4 hours of the addition, the resulting suspension is seeded every hour with SRFB hemi-tosylate monohydrate (starting when the addition begins, 4 seedings take place).

During the remaining 4 h of the addition, the resulting suspension is seeded every hour with Sorafenib tosylate ethanol solvate (therefore, starting 4 h after the addition begins, 4 seeding take place).

Once the addition is completed, the suspension is stirred at RT overnight.

The resulting suspension is filtered through a sinter funnel (porosity no 3). The solid was washed with EtOH abs. (2×50 mL) followed with a drying at 100° C. under vacuum (4 mbar). After 26 h (for 5 g of Sorafenib tosylate ethanol solvate), pure Sorafenib tosylate Form III was obtained as a white solid with an estimated extrapolated yield of 89%.

At 2 g scale, 1 hour extra at the end of the addition is necessary to obtain a complete conversion. At 25 g, due to the higher scale, the conversion was slower indicating a conversion of 50% 1 h after the end of the addition, then the reaction remained under stirring overnight. However the conversion should be complete with only some extra hours of slurrying. Stirring and scale factors have an important impact on the conversion rate.

The RT of our laboratory oscillates between 20° C. and 24° C. (humidity ranges 40-50%).

Preparation of 500 mL of EtOH 91% v/v: 455 mL of EtOH abs.+45 mL of deionized water.

EtOH abs (PANREAC, ref.: 141086.1214):
  EtOH: 99.5%
  $H_2O$: 0.5% (Karl Fischer analysis indicates 0.025%)

Water deionized technical grade (PANREAC, ref.: 212236.0716):
  pH: 7.2 (measured experimentally)

The reactions were monitored every hour by XRPD. The suspension samples were filtered and washed with EtOH 91% v/v before analyzing the resulting wet solid by XRPD. SRFB.TsOH Form I was not observed during all the process. The final product analyzed by XRPD using very sensitive conditions (32 min) indicated a pure SRFB.TsOH EtOH solvate crystal form.

The color of the suspension is an indicator of the conversion:

The initial light brown suspension of the SRFB free base in EtOH 91% v/v converted into a yellow suspension corresponding to SRFB hemi-tosylate (complete dissolution was not observed).

Then this yellow suspension converted with time into a beige color indicating advanced conversion.

The invention claimed is:

1. A process for preparing Sorafenib tosylate ethanol solvate of formula (I-EtOH):

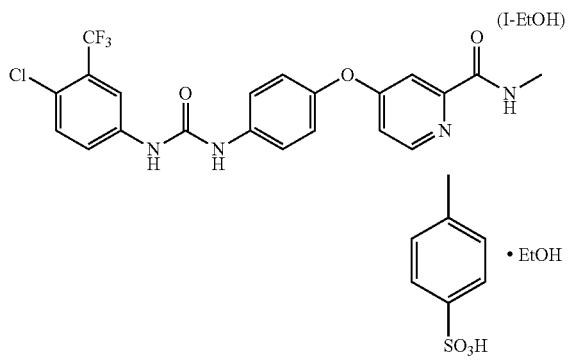

comprising:
a) providing a suspension of Sorafenib hemi-tosylate of formula (II) or hydrates thereof:

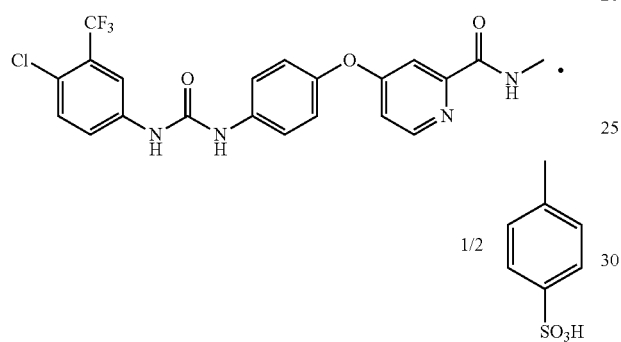

in ethanol 90-95% v/v,
b) adding paratoluenesulfonic acid or hydrates thereof to the suspension of step a),
c) stirring, and
d) isolating the product Sorafenib tosylate ethanol solvate of formula (I-EtOH).

2. The process of claim 1, wherein the Sorafenib hemi-tosylate of formula (II) or hydrate thereof is Sorafenib hemi-tosylate monohydrate.

3. The process of claim 1, wherein in step a) the provision of a suspension of Sorafenib hemi-tosylate of formula (II) or hydrates thereof is carried out by adding paratoluenesulfonic acid or hydrates thereof to a solution of Sorafenib base of formula (III):

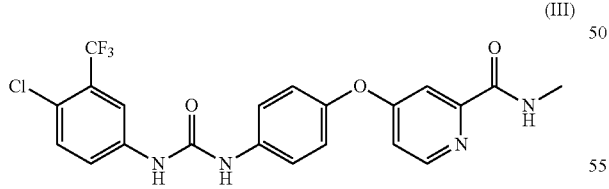

in ethanol 90-95% v/v.

4. The process of claim 1, wherein:
in step a) the provision of the suspension is carried out without the isolation of the compound Sorafenib hemi-tosylate of formula (II) or hydrates thereof; and
steps a), b), and c) are carried out in a one-pot process.

5. The process of claim 1, wherein step a) or steps from a) to d) are carried out in ethanol 90-95% v/v.

6. The process of claim 1, wherein from 7 to 17 volumes of ethanol 90-95% v/v are used in step a) or in steps from a) to d).

7. The process of claim 1, wherein in step b) the amount of paratoluenesulfonic acid added is from 0.7 to 1.2 equivalents.

8. The process of claim 7, wherein in step b) the addition of paratoluenesulfonic acid is performed by adding at first from 0.3 to 0.8 equivalents and then, adding about 2 hours later any remaining paratoluenesulfonic acid in one or more portions.

9. The process of claim 1, wherein in step b) the addition of paratoluenesulfonic acid or hydrates thereof is carried out portionwise or dropwise.

10. A process for preparing Sorafenib tosylate form III of formula (I):

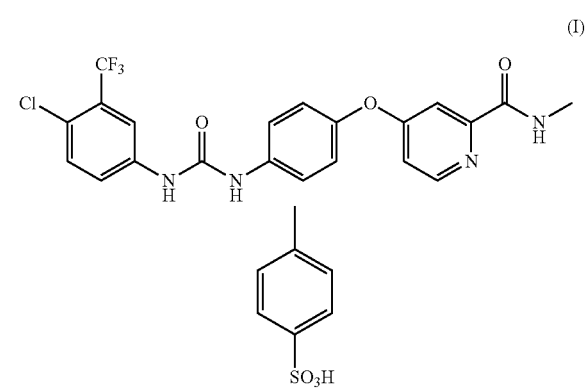

comprising:
a) preparing isolated Sorafenib tosylate ethanol solvate of formula (I-EtOH) according to the process of claim 1,
b) optionally,
  i) suspending in ethanol isolated Sorafenib tosylate ethanol solvate of formula (I-EtOH) as obtained in step a), and
  ii) stirring the suspension for a time of between 1 and 72 hours and then re-isolating the product of Sorafenib tosylate ethanol solvate of formula (I-EtOH), and
c) heating under vacuum isolated Sorafenib tosylate ethanol solvate of formula (I-EtOH) as obtained in step a) or step b).

11. The process of claim 10, wherein step c) is carried out at a temperature of from 95° C. to 105° C.

12. A process for preparing Sorafenib hemi-tosylate of formula (II) or hydrates thereof:

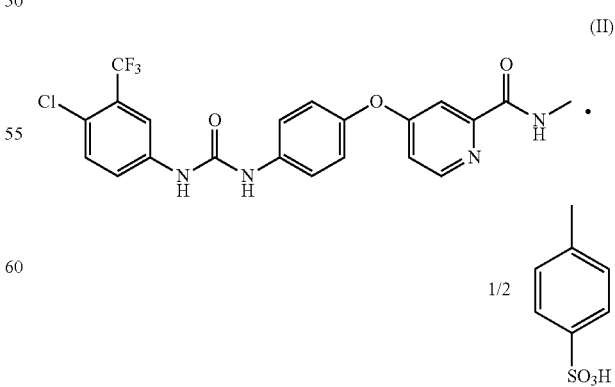

comprising adding paratoluenesulfonic acid or hydrates thereof to a solution of Sorafenib base of formula (III):

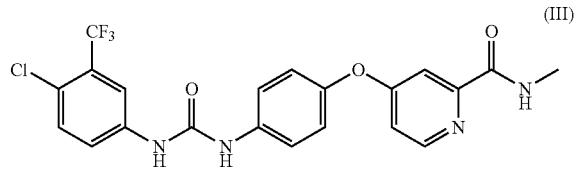 [SMILES: CNC(=O)c1cc(Oc2ccc(NC(=O)Nc3ccc(Cl)c(C(F)(F)F)c3)cc2)ccn1]

in ethanol 90-95% v/v, wherein Sorafenib tosylate form I does not appear during the process.

13. A process for preparing Sorafenib tosylate form III of formula (I):

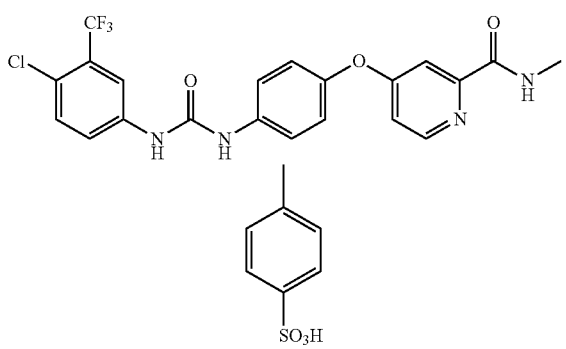

comprising:
a) suspending isolated Sorafenib tosylate ethanol solvate of formula (I-EtOH):

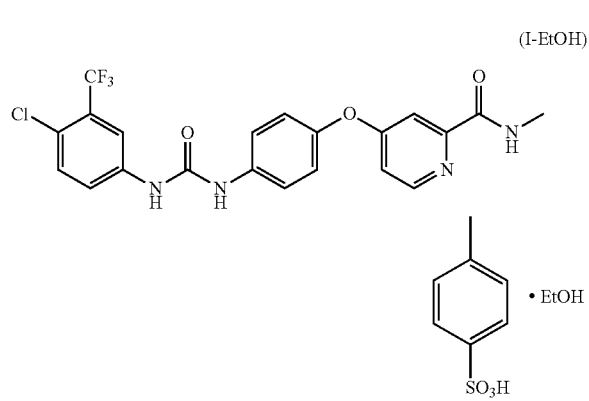

in ethanol,
b) stirring the suspension for a time of between 1 and 72 hours and re-isolating the product of formula (I-EtOH), and c) heating under vacuum the Sorafenib tosylate ethanol solvate of formula (I-EtOH) as obtained in step b).

14. The process of claim 13, wherein the heating in step c) is carried out at one temperature of between 95-105° C.

15. A process for preparing Sorafenib hemi-tosylate of formula (II) or hydrates thereof:

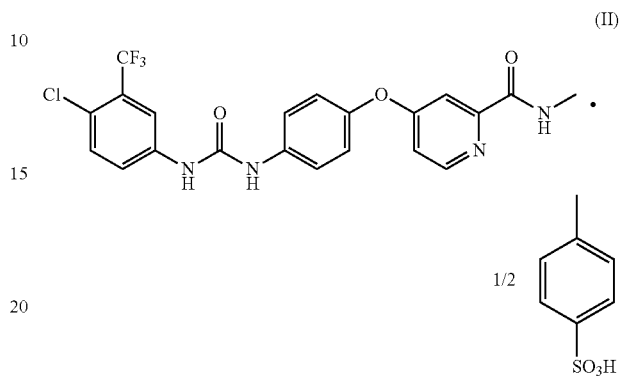

comprising adding from 0.55 to 0.8 molar equivalents of paratoluenesulfonic acid or hydrates thereof solubilized in a specific amount of water to a suspension of Sorafenib base of formula (III):

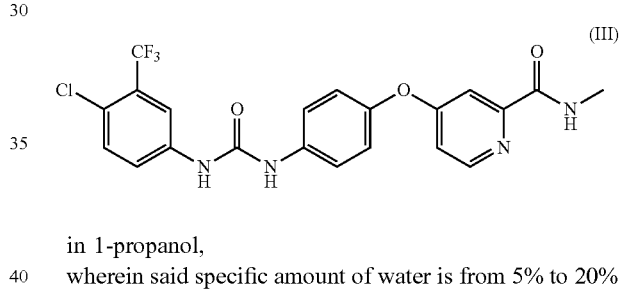

in 1-propanol,
wherein said specific amount of water is from 5% to 20% v/v compared to the volume of 1-propanol.

16. The process according to claim 1, wherein step a) is carried out by suspending Sorafenib hemi-tosylate in ethanol 90-95% v/v.

17. The process according to claim 13, wherein the product of the process contains no trace of Sorafenib tosylate form I.

18. The process according to claim 1, wherein the product of the process is not contaminated with Sorafenib tosylate form I.

* * * * *